(12) United States Patent
Prais et al.

(10) Patent No.: US 9,204,829 B2
(45) Date of Patent: Dec. 8, 2015

(54) MULTISTRIP CARTRIDGE

(71) Applicant: Bayer HealthCare LLC, Tarrytown, NY (US)

(72) Inventors: Eugene Prais, West Milford, NJ (US); Michael A. Botta, Manorville, NY (US); Narasinha Parasnis, Nanuet, NY (US); Serban Peteu, East Lansing, MI (US); John Creaven, Pearl River, NY (US); Simin Yao, Boonton Township, NJ (US)

(73) Assignee: Bayer HealthCare LLC, Whippany, NJ (US)

( * ) Notice: Subject to any disclaimer, the term of this patent is extended or adjusted under 35 U.S.C. 154(b) by 251 days.

(21) Appl. No.: 13/730,436

(22) Filed: Dec. 28, 2012

(65) Prior Publication Data

US 2013/0324822 A1    Dec. 5, 2013

Related U.S. Application Data

(60) Provisional application No. 61/653,838, filed on May 31, 2012.

(51) Int. Cl.
*A61B 5/145* (2006.01)
*G01N 33/52* (2006.01)
*G01N 33/487* (2006.01)
*A61B 5/15* (2006.01)

(52) U.S. Cl.
CPC ...... *A61B 5/14532* (2013.01); *G01N 33/48757* (2013.01); *G01N 33/521* (2013.01); *A61B 5/150358* (2013.01)

(58) Field of Classification Search
CPC combination set(s) only.
See application file for complete search history.

(56) References Cited

U.S. PATENT DOCUMENTS

| | | |
|---|---|---|
| 5,120,420 A | 6/1992 | Nankai et al. |
| 5,194,393 A | 3/1993 | Hugl et al. |
| 5,575,403 A | 11/1996 | Charlton et al. |
| 5,630,986 A | 5/1997 | Charlton et al. |
| 5,660,791 A | 8/1997 | Brenneman et al. |
| 5,738,244 A | 4/1998 | Charlton et al. |
| 5,759,364 A | 6/1998 | Charlton et al. |
| 5,798,031 A | 8/1998 | Charlton et al. |

(Continued)

FOREIGN PATENT DOCUMENTS

| | | |
|---|---|---|
| EP | 1321769 A1 | 6/2003 |
| EP | 2426493 A1 | 3/2012 |

(Continued)

OTHER PUBLICATIONS

International Search Report and Written Opinion for Application No. PCT/US2013/030897 dated Jun. 27, 2013.

(Continued)

*Primary Examiner* — Sam P Siefke
(74) *Attorney, Agent, or Firm* — Dugan & Dugan, PC

(57) ABSTRACT

A test meter for analyzing a body fluid sample applied to a test strip includes an outer housing having an opening, an actuator, and a cartridge positioned adjacent the outer housing. The cartridge further includes a dispensing member connected to the actuator, a plurality of stacked test strips biased toward the dispensing member, and a cartridge outer housing that is adjacent at least a portion of the dispensing member. Each time the actuator is actuated, the dispensing member is rotated to cause movement of one test strip from the plurality of stacked test strips through the opening, and another test strip is biased toward the dispensing member.

15 Claims, 21 Drawing Sheets

(56) References Cited

U.S. PATENT DOCUMENTS

| | | |
|---|---|---|
| 5,810,199 A | 9/1998 | Charlton et al. |
| 5,854,074 A | 12/1998 | Charlton et al. |
| 5,856,195 A | 1/1999 | Charlton et al. |
| 6,997,343 B2 | 2/2006 | May et al. |
| 7,449,148 B2 | 11/2008 | Matsumoto et al. |
| 8,105,536 B2 | 1/2012 | Charlton |
| 2002/0057993 A1* | 5/2002 | Maisey et al. .............. 422/82.01 |
| 2004/0178216 A1 | 9/2004 | Brickwood et al. |
| 2007/0173739 A1 | 7/2007 | Chan |
| 2010/0087754 A1 | 4/2010 | Rush et al. |
| 2013/0324822 A1 | 12/2013 | Prais et al. |

FOREIGN PATENT DOCUMENTS

| | | |
|---|---|---|
| WO | 2005046477 A2 | 5/2005 |
| WO | 2009120664 A2 | 10/2009 |

OTHER PUBLICATIONS

International Search Report and Written Opinion for Application No. PCT/US2012/0072118 dated Mar. 28, 2013.

* cited by examiner

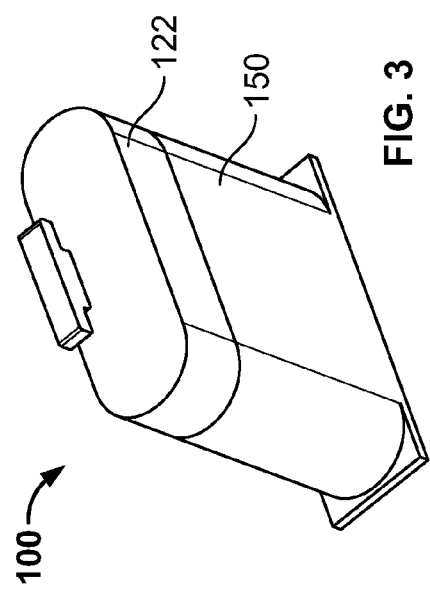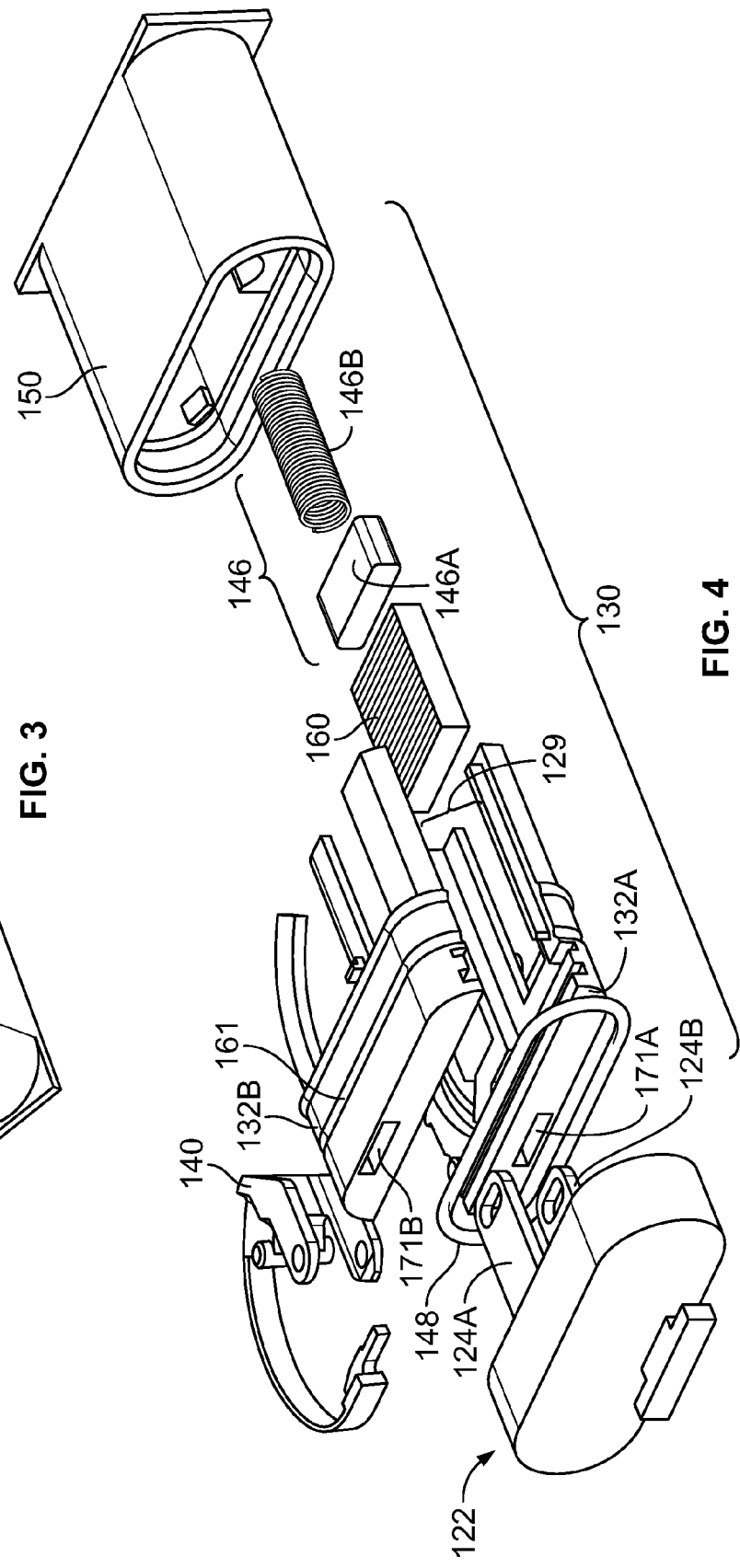

MULTISTRIP CARTRIDGE

CROSS-REFERENCE TO RELATED APPLICATIONS

The present application claims the benefit of the filing date of U.S. Provisional Patent Application No. 61/653,838 filed May 31, 2012, the disclosure of which is hereby incorporated herein by reference.

BACKGROUND OF THE INVENTION

The present invention relates to fluid monitoring devices and the distribution of test strips stored within the fluid monitoring devices.

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration level. An irregular blood glucose level can be brought on by a variety of reasons, including illness, such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables the users to conveniently test their blood glucose levels wherever the user may be. The glucose testing device includes a test strip to harvest the blood for analysis. One type of test strip is the electrochemical test strip. The electrochemical test strip includes a regent designed to react with glucose in the blood to create an oxidation current at electrodes disposed within the electrochemical test strip which is directly promotional to the user's blood glucose concentration. Such a test strip or biosensor is described in U.S. Pat. Nos. 5,120,420, 5,660,791, 5,759,364, and 5,798,031, each of which is incorporated herein in its entirety. Another type of sensor is an optical test strip, which incorporates a reagent designed to produce a colorimetric reaction indicative of a user's blood glucose concentration level. The calorimetric reaction is then read by a spectrometer incorporated into the testing device. Such an optical test strip is described in U.S. Pat. No. 5,194,393, which is incorporated herein by reference in its entirety.

In order to check a person's blood glucose level, a drop of blood is obtained from the person's fingertip using a lancing device, and the blood is harvested using the test strip. The test strip, which is inserted into a testing unit, is brought into contact with the blood drop. The test strip draws the blood, via capillary action, inside the test strip and the ensuing electrochemical reaction is measured by the test unit, which then determines the concentration of glucose in the blood. Once the results of the test are displayed on a display of the test unit, the test strip is discarded. Each new test requires a new test strip.

Referring now to FIGS. 1 and 2, examples of a testing device 10 and a package 30 of test strips 12 ("test strip pack") are shown, respectively. The test strip pack 30 is designed to be housed within the testing device 10. Prior to each test, a collection area 14 of an individual test strip 12 is pushed by a mechanism within the testing device 10 through its packaging and is extended from the testing device 10 through a slot 16 for harvesting a sample of blood. The testing device 10 includes a slider 18 for advancing the test strip 12. In FIG. 1, a test strip 12 is shown extending from the testing device 10. The collection area 14 extends from the testing device 10, while a contact area, disposed at the opposite end of the test strip 12, shown in FIGS. 1 and 2, remains inside the testing device 10. The contact area includes terminals that electrically couple the electrodes to a meter disposed within the testing device 10 for measuring the oxidation current produced at the electrodes by the reaction of glucose and the reagent. The test unit includes a display 20.

Referring now to FIG. 2, test strips 12 are shown disposed in the test strip pack 30. The test strip pack 30 is made up of a circular disk 32 having only ten individual compartments (blisters) 34 arranged radially. The disk is made from an aluminum foil/plastic laminate which is sealed to isolate the sensor from ambient humidity and from other sensors with a burst foil cover 36. Each test strip 12 is kept dry by a desiccant located inside a desiccant compartment 37 disposed adjacent to the compartment 34.

To retrieve a test strip, a mechanism disposed within the testing device 10, such as a knife, is driven down through the burst foil into an individual elongated compartment 34 at the end closest to the hub of the disk 32 and then moved radially toward the perimeter of the blister 34. In doing so, the knife engages the contact area 38 (fish tail) of the sensor in that compartment. Radial travel of the knife pushes the tip of the sensor out through the burst foil 36 and through parts of the testing device 10 such that the collection area 14 of the sensor 12 is completely out of the testing device 10 and ready to receive a fluid test sample such as blood. For this stage, it is essential that the bond between the base and lid of the test strip withstand the sheer forces generated when the test strip bursts out through the foil 36. This method of providing a test strip ready for use is more fully described in U.S. Pat. No. 5,575,403, which is incorporated herein by reference in its entirety.

Further details of the operational and mechanical aspects of the testing device 10 and test strip pack 30 are more fully described in U.S. Pat. Nos. 5,575,403, 5,630,986, 5,738,244, 5,810,199, 5,854,074, and 5,856,195, each of which are hereby incorporated by reference in their entireties.

A drawback associated with this flat array of testing devices is the large area that is occupied. The size of testing devices that internally house such a flat array package constrains the size of the package (i.e., the number of test strips), thus making it difficult to increase the number of test strips per package. Accordingly, there exists a need for a testing system capable of storing and dispensing numerous test strips.

SUMMARY OF THE INVENTION

According to one aspect of the embodiment disclosed herein, a test meter for analyzing a body fluid sample applied to a test strip includes an outer housing having an opening; an actuator positioned adjacent the outer housing; and a cartridge for dispensing test strips positioned adjacent the outer housing. The cartridge further includes a dispensing member connected to the actuator; a plurality of stacked test strips biased toward the dispensing member; and a cartridge outer housing is adjacent at least a portion of the dispensing member. Each time the actuator is actuated, the dispensing member is rotated to cause movement of one test strip from the plurality of stacked test strips through the opening, and another test strip is biased toward the dispensing member.

In one alternative embodiment, the dispensing member is a flexible arm having a first end and a second end. When the actuator is actuated, the dispensing member moves one test strip across the top of the stack of strips through the opening.

In one embodiment, the dispensing member has a first end and a second end. The first end is a free end contacting the test strip and the second end is a fixed end. The free end rotates about the fixed end when the actuator is actuated.

In another embodiment, the dispensing member is a rotatable block that has a recess for receiving one test strip from the plurality of stacked test strips. When the actuator is actuated, the block rotates and moves the test strip received within the recess away from the stack of test strips.

In another embodiment, the dispensing member and the plurality of test strips are positioned within the outer housing.

In still another embodiment, only the dispensing member is positioned within the outer housing, and the cartridge is connected to the outer housing.

In another embodiment, the test meter is able to analyze the fluid sample while the dispensed test strip remains in the opening.

In another embodiment, the cartridge further includes an interior cartridge housing, which is joined with the outer housing. A cover may be connected to and engaged with the dispensing member. The cover causes the dispensing member to move.

In still another embodiment, the cartridge further comprises a channel for receiving the dispensing member and providing a pathway that allows the dispensing member to move between a first position and a second dispensing position within the channel.

In another embodiment, the cartridge further includes a cover removably joined together with the outer casing and an interior cartridge housing for housing the dispensing member. The interior cartridge housing further includes a test strip storage area for storing the plurality of stacked test strips therein, and each of the test strips has edges aligned with one another. Alternatively, each of the stacked test strips have an outer edge and each of the outer edges are aligned with one another within the test strip storage area. A seal may also extend between the interior cartridge housing and the outer housing.

In another aspect of the presently disclosed embodiment, a method for testing a fluid sample deposited on a test strip includes the steps of actuating a dispensing member contained in a test meter; providing the fluid sample on the exposed portion of the test strip; analyzing the fluid sample while the opposed edge of the one test strip remains; and biasing another test strip toward the dispensing member. The step of actuating includes moving the dispensing member from a stationary position to a dispensing position. One test strip in contact with the dispensing member and stored within a stack of test strips in the test meter is also moved toward an opening in the test meter during the actuating step. At least one edge of the one test strip is exposed and an opposed edge of the test strip remains within the opening when the test strip is moved toward the opening.

In an alternative embodiment, the dispensing member includes a movable arm that has a fixed end and a free end. The free end is in contact with the one test strip. The dispensing member may rotate about a fixed point when it moves the test strip from a first position to a second position.

In another embodiment, the dispensing member is a movable block capable of moving the test strip from a first position to a second position. Alternatively, the block has a recess for receiving one strip.

In still another embodiment, the cartridge further includes a cover connected to the actuator and the dispensing member further includes a cover. The dispensing member has a first end and a second dispensing end. The dispensing member has a flexible arm capable of moving between a first position and a second position each time the actuator is actuated.

In another aspect of the presently disclosed embodiments, a cartridge for use in a test meter includes an outer casing; a cover removably joined together with the outer casing; and a dispensing assembly seated within the outer casing. The dispensing assembly further includes a test strip storage area for storing a plurality of stacked test strips therein; a dispensing member movably connected to the cover and contacting a single test strip of the plurality of test strips; and a biasing member for moving the plurality of stacked strips toward the dispensing member. Each of the test strips has edges aligned with one another and the dispensing member rotates between a first "rest" position and a second "dispensing" position. The dispensing member moves the one test strip through the opening when the cover is moved away from the dispensing assembly.

In accordance with yet another aspect of the presently disclosed embodiment, a test meter for analyzing a body fluid sample applied to a test strip includes an outer housing having an opening, an actuator positioned adjacent the outer housing, a cartridge for storing a plurality of stacked test strips for distribution through the opening, and a dispensing member movably connected to the actuator. The plurality of stacked test strips are biased toward the dispensing member so that each time the actuator is actuated, the dispensing member is rotated to cause movement of one test strip from the plurality of stacked test strips through the opening, and another test strip from the plurality of stacked test strips is biased toward the dispensing member.

In an alternative embodiment of this aspect, the test meter is a flexible arm having a first end a second end. When the actuator is actuated, the dispensing member moves one test strip across a top of the plurality of stacked strips and through the opening in the outer housing. The dispensing member may have a first end and a second end. The first end of the dispensing member may be a free end that comes into contact with the test strip and the second end may be a fixed end. The free end may rotate about the fixed end when the actuator is actuated.

In another alternative embodiment of this aspect, the dispensing member is a rotatable block having a recess for receiving one test strip from the plurality of stacked test strips. When the actuator is actuated, the block may rotate so as to move the test strip received within the recess away from the stack of test strips.

In another embodiment, the dispensing member and plurality of test strips are positioned within the outer housing. Alternatively, only the dispensing member is positioned within the outer housing, and the cartridge is connected to the outer housing.

In an alternative embodiment, the test meter is able to analyze the fluid sample while the dispensed test strip remains within the opening.

In another embodiment, the cartridge may further comprise an interior cartridge housing joined with the outer housing, a covering element, and a channel. The covering element may have a connecting portion engaged with the dispensing member. Alternatively, the covering element may be removably joined together with the outer casing. The covering element may cause the dispensing member to move between a first position and a second position. The channel may be constructed and arranged to receive the dispensing member and to provide a pathway that allows the dispensing member to move between a first position and a second dispensing position within the channel. The interior cartridge housing may further include a test strip storage area for storing the plurality of stacked test strips therein, wherein each of the test strips have edges aligned with one another.

In another embodiment, each of the stacked test strips have an outer edge, and each of the outer edges are aligned with one another within the test strip storage area.

In another alternative embodiment, a seal extends between the interior cartridge housing and the outer housing.

In accordance with another aspect of the presently disclosed embodiment, there is a method for testing a fluid sample deposited on a test strip including biasing a first test strip of a plurality of test strips contained in a stacked configuration in a test meter toward a dispensing member; moving the dispensing member across the plurality of test strips so as to move the first test strip toward an opening in the test meter and so that at least one edge of the one test strip is ejected through the opening in the test meter and an opposed edge of the test strip remains within the test meter; providing the fluid sample on the exposed portion of the test strip; analyzing the fluid sample while the opposed edge of the one test strip remains; and biasing a second test strip of the plurality of test strips toward the dispensing member once the first test strip has been ejected.

In an alternative embodiment, the step of moving the dispensing member comprises rotating the dispensing member about a fixed point. Alternatively, the step of moving may include rotating a movable block that is capable of moving the test strip from a first position to a second position.

In another alternative embodiment, the method further comprises the step of placing the dispensing member in contact with the test strip. The step of moving the dispensing member further may further include rotating a fixed end of the dispensing member about a fixed point so as to allow a free end of the dispensing member to move the test strip. Alternatively, the step of moving the dispensing member may include moving a flexible arm between a first position and a second position.

In accordance with another aspect of the presently disclosed embodiment, there is a cartridge for storing a plurality of stacked test strips in a test meter. The cartridge includes an outer casing, a covering element removably joined together with the outer casing, and a dispensing assembly seated within the outer casing. The dispensing assembly may further comprise a test strip storage area for storing the plurality of stacked test strips and a dispensing member. Each of the test strips may have opposed edges aligned with one another. The dispensing member may be movably connected to the cover and contact a single test strip of the plurality of test strips. The plurality of stacked strips may be biased toward the dispensing member, and the dispensing member may rotate between a first rest position and a second dispensing position. The dispensing member moves the one test strip through the opening when the cover is moved away from the dispensing assembly. The dispensing member may be an elongated member having a first free end and a second fixed end, the dispensing member moving about the second end.

In an alternative embodiment, the dispensing member is an elongated member having a first free end and a second fixed end. The dispensing member moves about the second end.

BRIEF DESCRIPTION OF THE DRAWINGS

FIG. 3 is a cartridge for use in a multistrip meter in accordance with one embodiment of the invention.

FIG. 4 is an exploded perspective view of the cartridge shown in FIG. 3.

DETAILED DESCRIPTION

Figure 1:
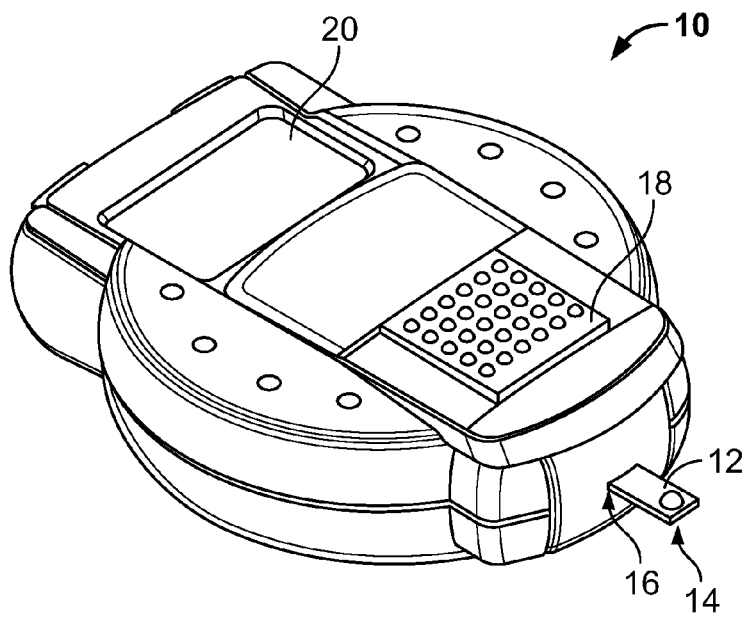
FIG. 1 is a perspective view of a prior art test meter.
Figure 2:
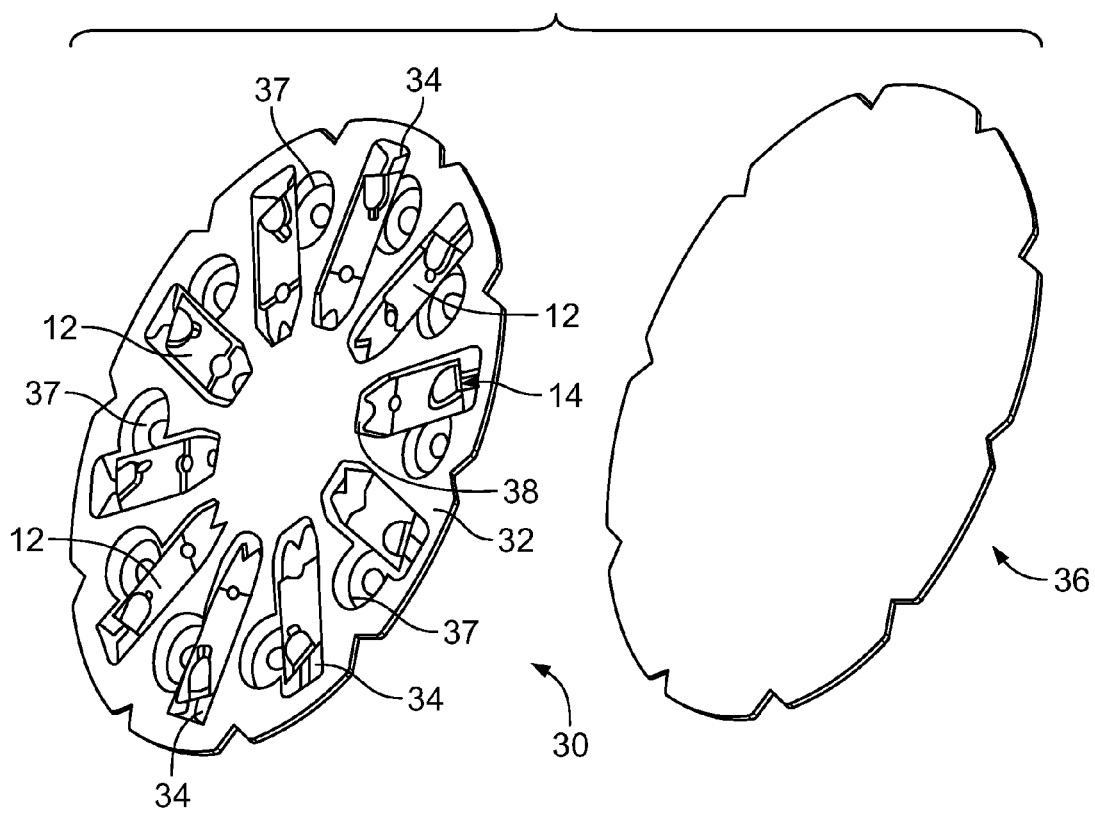
FIG. 2 is a perspective view of a prior art cartridge that can be used in the meter shown in FIG. 1.

The following discussion describes, in detail, various aspects and embodiments of the present invention. This discussion should not be construed as limiting the invention to those particular aspects or embodiments. Rather, practitioners skilled in the art will recognize numerous other aspects and embodiments as well, which are within the scope of the present invention.

In describing the preferred embodiments of the present invention illustrated in the drawings, specific terminology will be used for the sake of clarity. For purposes of explanation, the invention is generally described herein with regard to glucose test meters and test strips. However, the present invention is not intended to be limited to the specific terms so selected, and it is to be understood that each specific term includes all technical equivalents that operate in a similar manner to accomplish a similar purpose. The presently disclosed meter may contain test strips designed to determine the concentration of other analytes in other types of samples. For example, test strips may alternatively measure lipid profiles (e.g., cholesterol, triglycerides, low-density lipoprotein (LDL) and high-density lipoprotein (HDL)), microalbumin, hemoglobin A1c, fructose, lactate, bilirubin, or other analytes. The analytes may be in, for example, a whole blood sample, a blood serum sample, a blood plasma sample, or body fluids like interstitial fluid (ISF) and urine.

Referring now to FIG. 3, there is shown a perspective view of a cartridge 100 for use in a multistrip meter in accordance with one embodiment of the invention. Cartridge 100 can be used to both store and dispense a plurality of the test strips or biosensors within the cartridge 100. As shown, cartridge 100 has an elongated oblong shape and extends vertically upward.

Turning to FIG. 4, an exploded perspective view of the components of cartridge 100 is shown. In this embodiment, cartridge 100 includes three major components: cover portion 122, dispensing assembly 130, and outer housing 150. Each of these components will be further discussed in greater detail herein.

Figure 5:
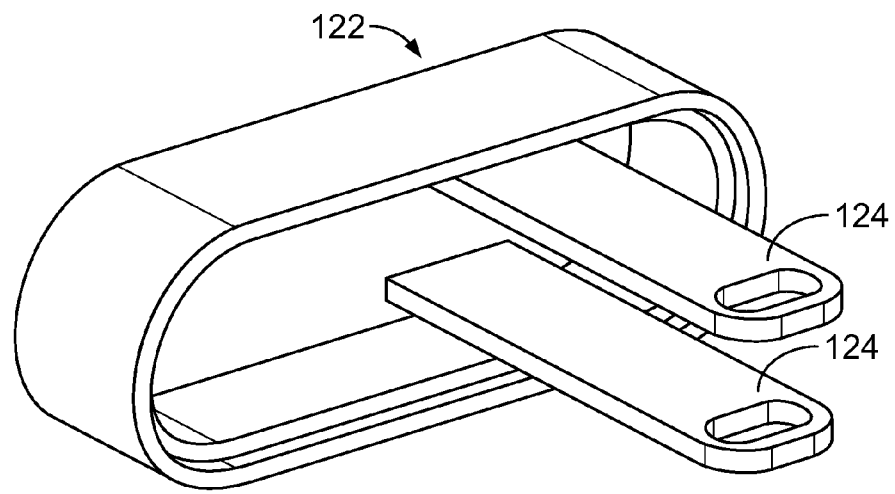
FIG. 5 is a perspective view of a cover component of the cartridge shown in FIG. 4, in accordance with one embodiment.
Figure 5A:
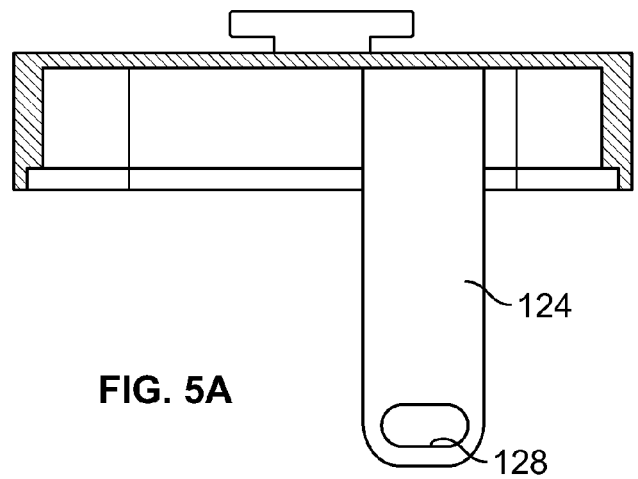
FIG. 5A is a front plan view of FIG. 5.
Figure 5B:
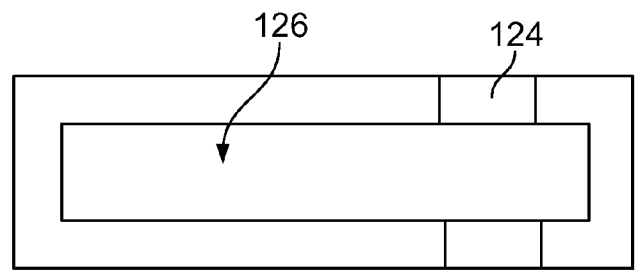
FIG. 5B is a bottom plan view of FIG. 5.

Cover portion 122 of cartridge 110 is shown in greater detail in FIGS. 5-5B. In one embodiment, cover portion 122 is an elongated and rounded cap (FIG. 4) with connection members 124 that extend away from cover portion 122 and also toward dispensing assembly 130. An aperture 128 (FIG. 5A) is positioned on a lower portion of connection members 124 that extend closer to dispensing assembly 130, away from cover portion 122.

With reference to FIGS. 5A and 5B, a cavity or recess 126 is formed within the interior portion of cover portion 122. As shown, a thickness of the material comprising the cover portion 122 circumscribes the perimeter of the cover portion 122 so as to form cavity 126. In one embodiment, cover portion 122 can also function to actuate dispensing assembly 130 (FIG. 4) so that test strips can be dispensed from the dispensing assembly. Cover portion 122, which cooperates with O-ring 148 on the dispensing assembly 130, may also function to help provide an airtight seal for dispensing assembly 130 so as to prevent the interior portion of dispensing assembly 130 from becoming contaminated by a user or the outer atmosphere.

Turning now to the dispensing assembly 130, shown in FIG. 4, dispensing assembly also includes three primary components: an interior cartridge housing 129 (FIG. 6) having a first half 132A joined to a second half 132B; a dispensing member 140 (FIG. 7) and a spring loaded block 146 (FIG. 7); provided within interior cartridge housing 129. Dispensing assembly 130 is capable of both storing a plurality of stacked test strips 160 and then dispensing each of the plurality of test strips 160, stored within the cartridge 100, one at a time. In one embodiment, dispensing assembly 130 is capable of storing at least 45 test strips, but any number of test strips may be stored therein.

Figure 6:
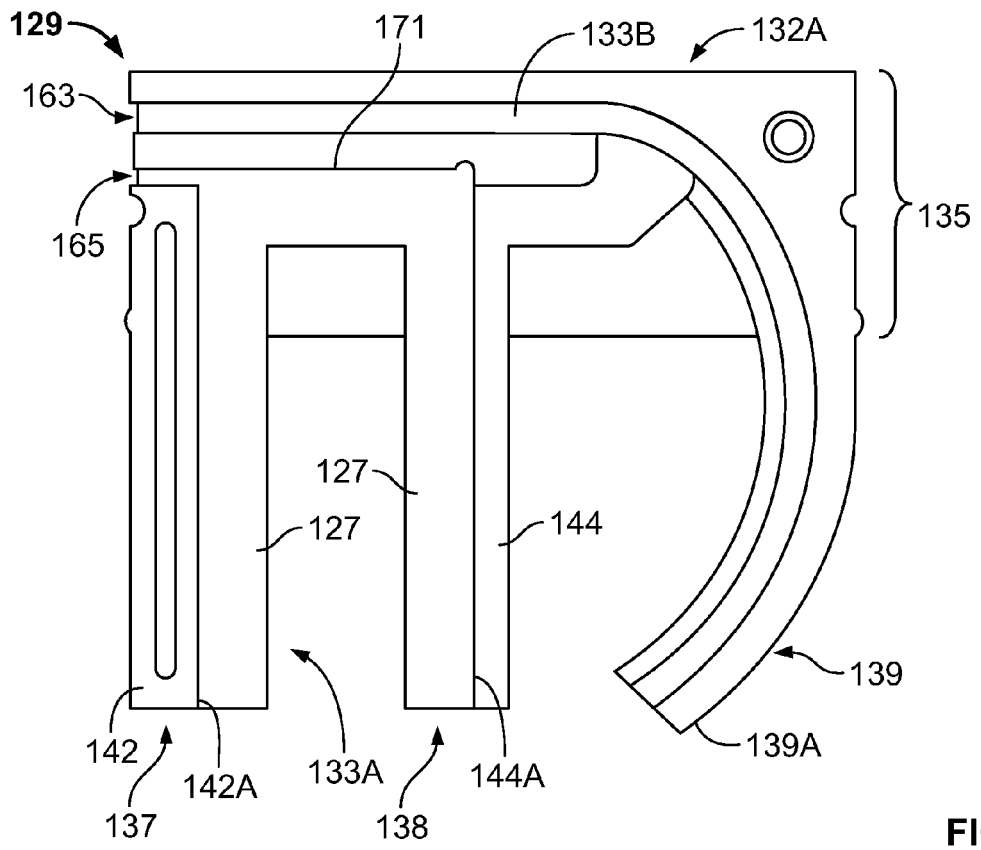
FIG. 6 is a housing component of the cartridge shown in FIG. 3, in accordance with one embodiment of the invention.

With reference to FIGS. 4 and 6, first half 132A of the interior cartridge housing 129 of dispensing assembly 130 has a main body 135, as well as first 137, second 138, and third 139 protruding legs extending away from the main body 135. First protruding leg 137 extends vertically away from the main body 135 and includes a raised portion 142 with an edge 142A. Similarly, second protruding leg 138 has a raised portion 144 with edge 144A. Edges 142A and 144A form a recess 133A for receiving a plurality of test strips 160 (FIG. 4). Third protruding leg 139 also extends vertically away from main body 135. Third protruding leg 139 is rounded and includes a channel 133B that is constructed and arranged to receive dispensing member 140. Channel 133B extends from a first end 139A of the third leg 139 across a length of main body 135 and terminates in an opening 163S in main body 135. Channel 133B provides a pathway for the dispensing member 140 to move therein.

Figure 7:
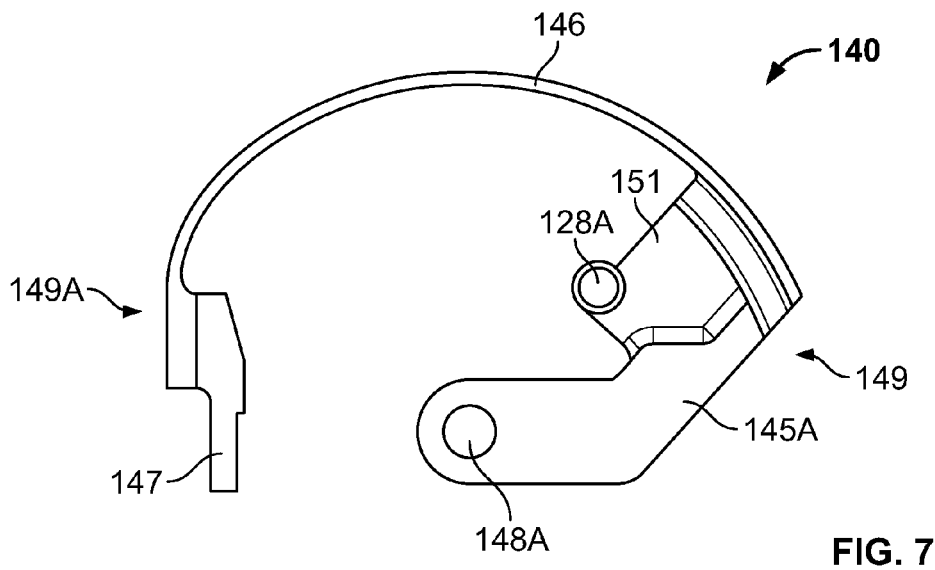
FIG. 7 is a dispensing member component of the cartridge shown in FIG. 4, in accordance with one embodiment of the invention.
Figure 7A:
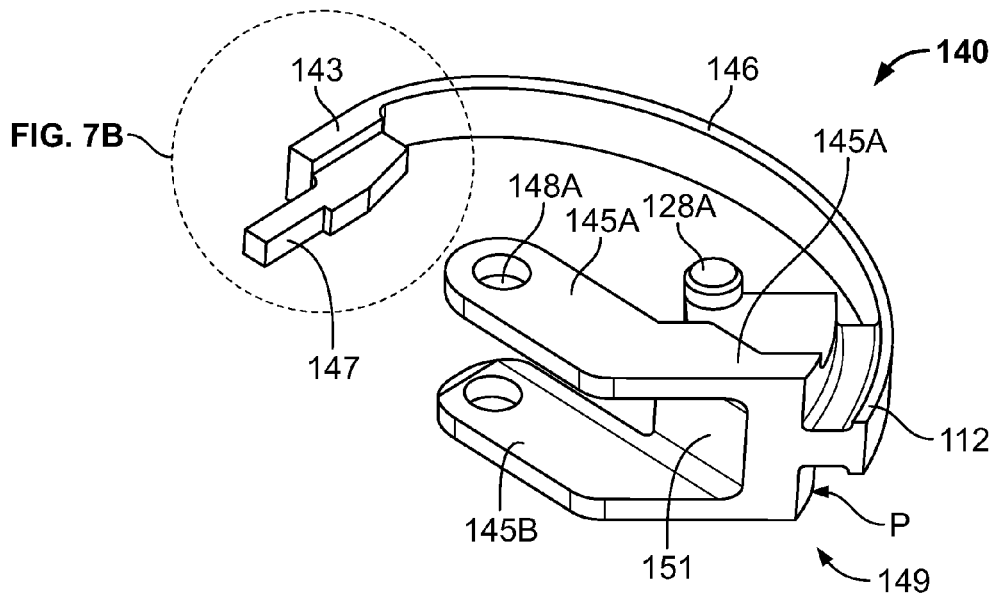
FIG. 7A is a front perspective view of the component shown in FIG. 7.
Figure 7B:
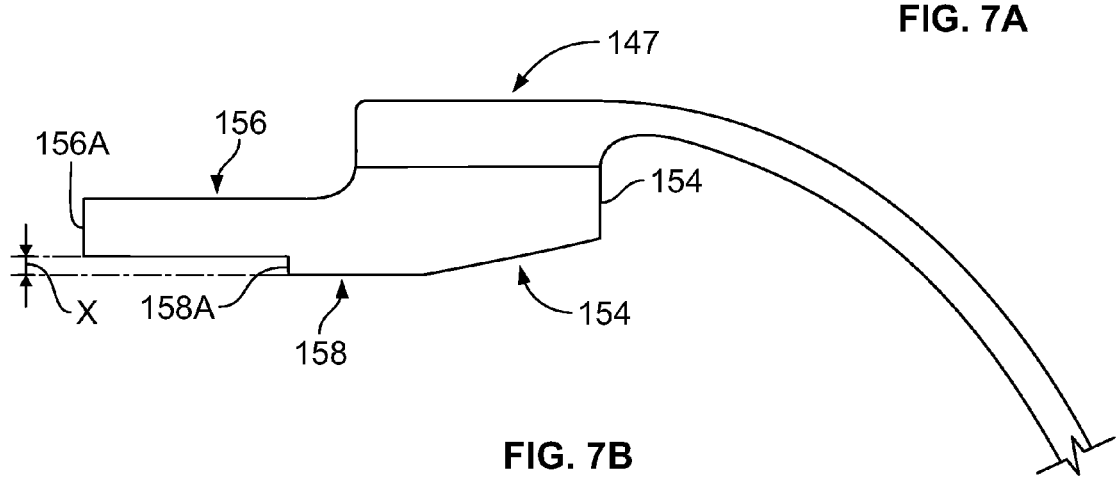
FIG. 7B is an exploded view of FIG. 7A.

Dispensing assembly 130 further includes dispensing member 140 shown in FIGS. 7, 7A, and 7B, which has an overall rounded shape. Turning first to FIGS. 7 and 7A, respectively, a front plan view and front perspective view of the dispensing member 140 is shown. As shown, dispensing member 140 has a rigid first end 149 and a rigid second end 149A, but the arm portion 146 extending between the first and second ends 149,149A is flexible. The flexibility of the arm portion 146 helps dispensing member 140 more easily fit within and move through channel 133B. As best seen in FIG. 7A, at first end 149, arm portion 146 has an I-beam shaped profile. As will be discussed in more detail herein, edge 112 of the I-beam profile helps to ensure that the arm 140 travels along a pre-selected path defined by the shape of channel 133B.

There is a hinge connection at first end 149 of dispensing member 140 that has a first hinge arm 145A and second hinge arm 145B that is separated by a hinge main body 151. Second end 152 of dispensing member 140 has a finger 147 for causing test strips 160 stored within the dispensing assembly 130 to be ejected from the dispensing assembly 130. Referring to FIG. 7B, finger 147 can include three sections: a front section 156, a rear section 154, and an intermediate section 158 positioned between the respective front and rear sections 154,156. Each of the front, rear, and intermediate sections 154,156,158 may have differing thicknesses. As shown, intermediate section 158 has an edge 158A having a height X. The height X can vary but, in this embodiment, is directly related to the size of a test strip. In one example, the height X is slightly less than the height of the test strip for distribution to a user. For example, if a test strip has a height of 0.43 mm, the height X of edge 158A can be slightly less than 0.43 mm, such as 0.35 mm. It is to be appreciated that this embodiment provides only one example and that any size of test strip and height X of edge 158A that is less than the height of the test strip is contemplated by the scope of the present invention. In preferred embodiments, the test strip ranges from 0.30 mm to 0.50 mm and the height X of edge 158A can range from 0.29 mm to 0.49 mm. It is, of course, to be appreciated that any size of test sensor and corresponding height X of edge 158A can be used. In alternate embodiments, it may also be desirable for the height to be slightly greater than the height of the test strip.

Figure 8:
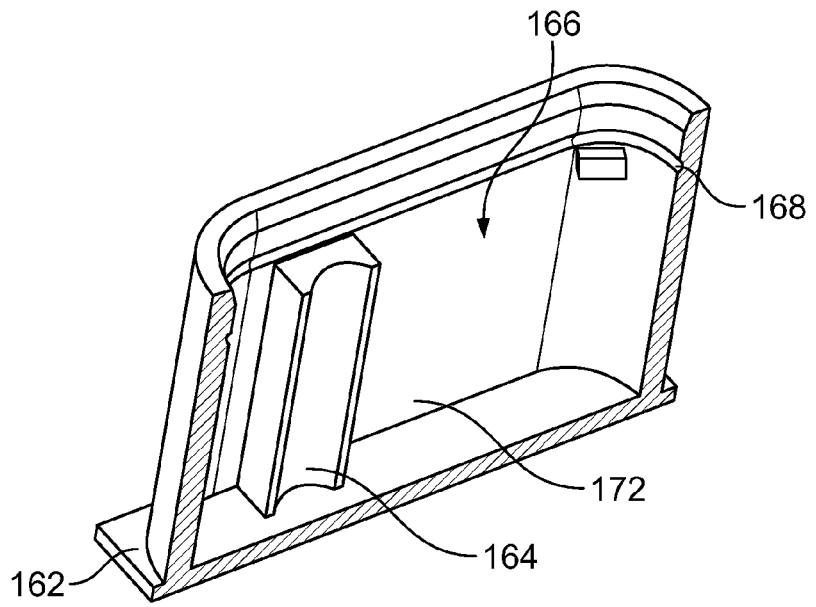
FIG. 8 is a cross-sectional perspective view of the outer housing component of the cartridge shown in FIG. 4, in accordance with one embodiment.
Figure 8A:
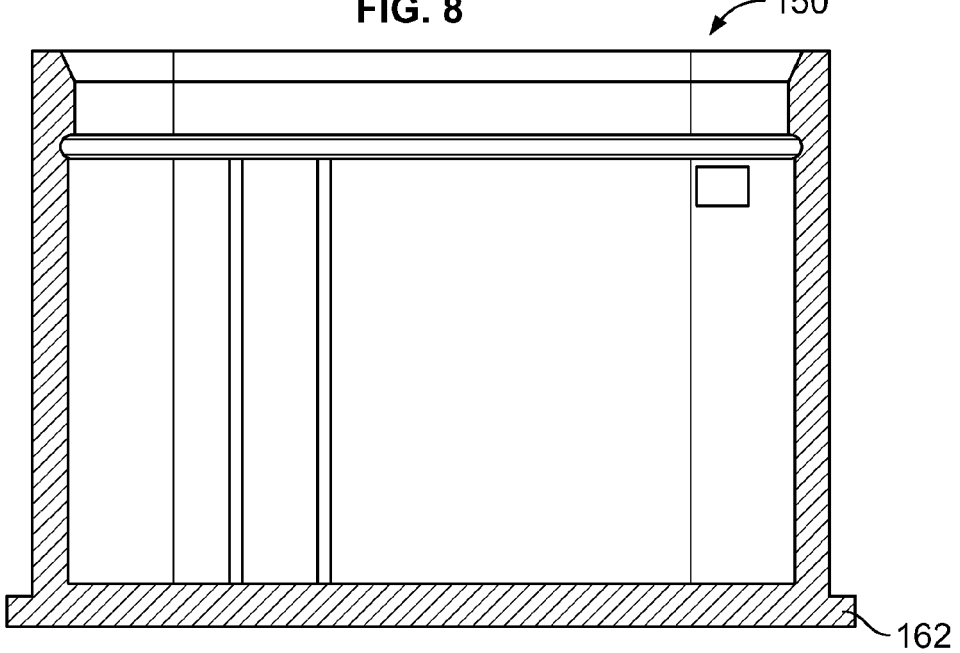
FIG. 8A is a front plan view of the cartridge shown in FIG. 4.
Figure 8B:
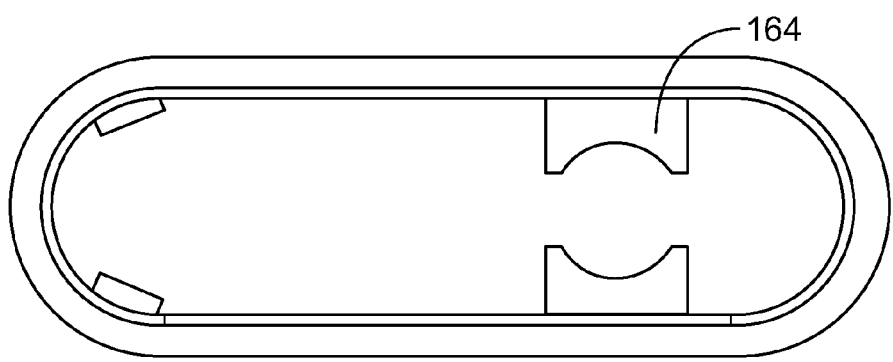
FIG. 8B is a top plan view of the cartridge shown in FIG. 4.

Turning now to FIGS. 8 and 8A, there is shown a perspective cross-sectional view and a cross-sectional view of outer housing 150. In this embodiment, outer housing 150 includes a base 162 and spring housing 164. The interior 166 of outer housing 150 is primarily a hollow housing for receiving dispensing assembly 130. There is also a first groove 168 extending along the interior surface 172 for receiving dispensing assembly 130, as will be discussed in more detail herein. FIG. 8B is a top plan view of outer housing 150 looking into the interior 166 of outer housing 150.

Figure 6A:
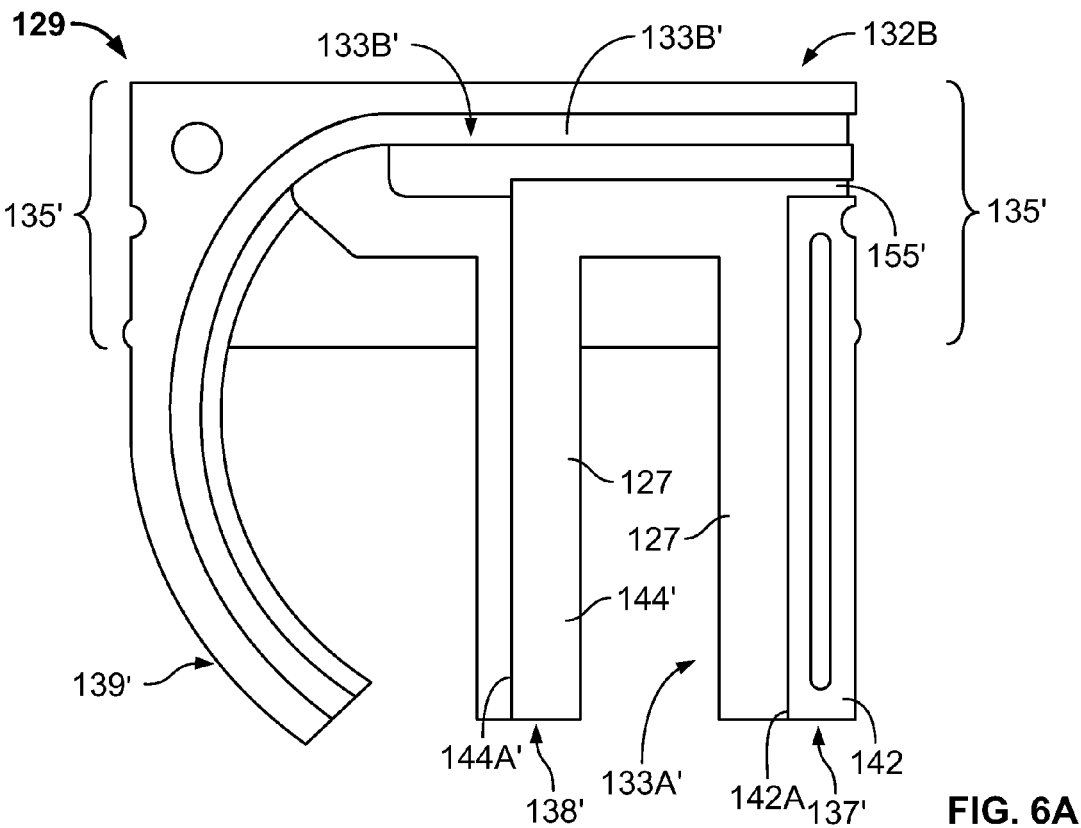
FIG. 6A is a housing component of the cartridge shown in FIG. 4, in accordance with one embodiment of the invention.

The components of cartridge 100 can be easily assembled together. Turning first to the dispensing assembly 130 (FIGS. 4,6,6A), first and second halves 132A,132B of the interior cartridge housing 129 may be joined together. Before doing so, test strips 160 and dispensing member 140 may be provided therein. Dispensing member 140 may be provided within the channels extending through interior cartridge housing 129. Test strips 160 are provided within recess 133A in a lengthwise direction so that each of the edges of the test strips are aligned with one another. Once the interior cartridge housing 129 is fully assembled, O-ring 148 may be provided within a groove 161 that extends around the perimeter of the assembled first and second halves 132A,132B of the interior cartridge housing 129. O-ring 148 is commonly comprised of a rubber material that can help to form a seal. Cover portion 122 of the cartridge 100 may then be joined to interior cartridge housing 129.

The combined cover portion 122 and interior cartridge housing 129 may then be positioned within outer housing 150, thereby forming a completed cartridge 100. As shown, O-ring 148 cooperates with the cover portion 122 to create an airtight seal when the cover portion 122 is in a closed position. In one embodiment, O-ring 148 is compressed when cover portion 122 is removably joined to outer housing 150. This can help to prolong the freshness of the test strips in the interior cartridge housing 129 and minimize, if not eliminate, the possibility of the stored test strips being contaminated while contained in cartridge 100. Furthermore, this configuration can help to minimize contamination of the plurality of test strips 160 stored within the interior cartridge housing 129, as well as promote a moisture-impervious environment.

Figure 9:
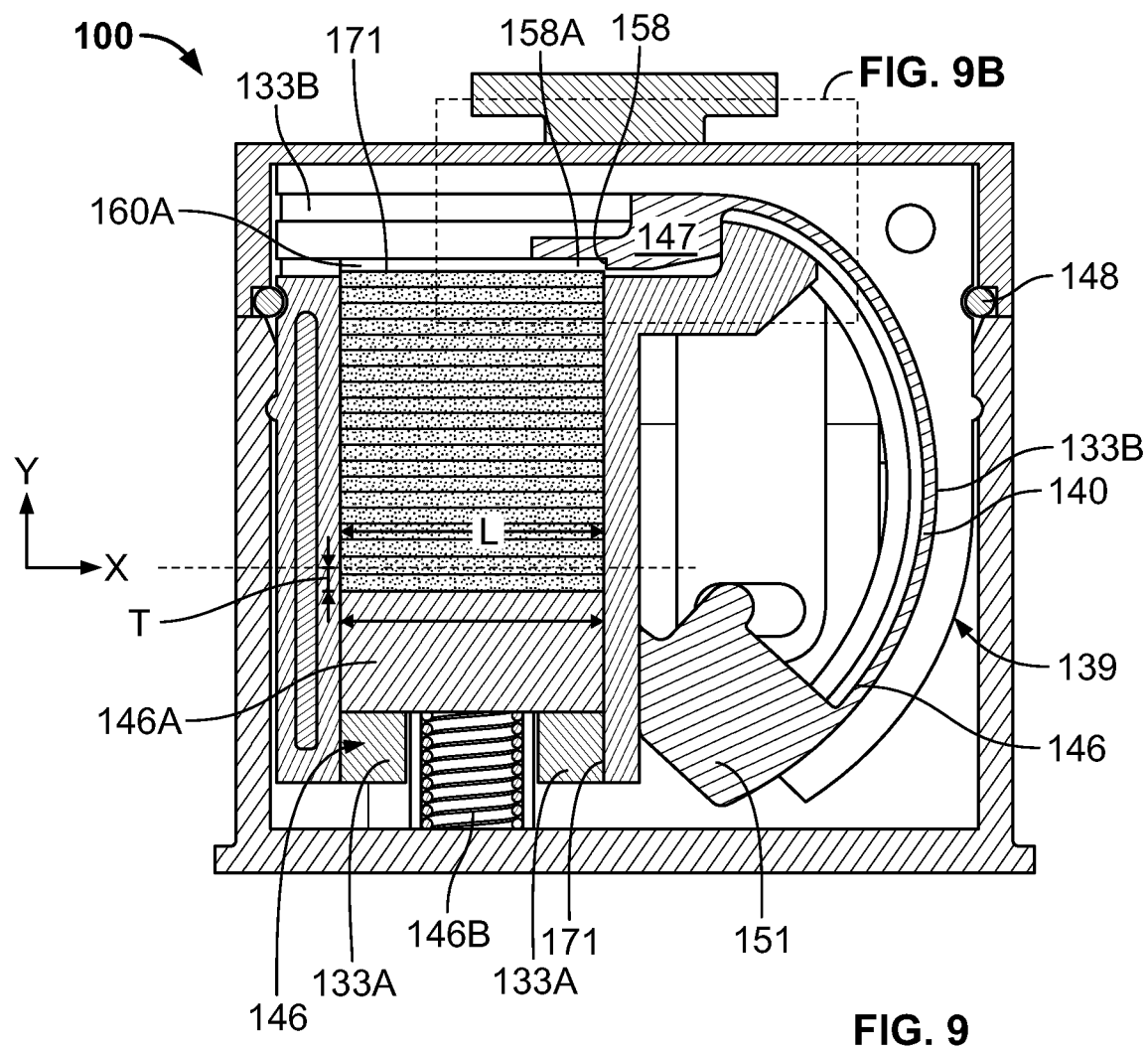
FIG. 9 is a cross sectional view of the cartridge shown in FIG. 3.
Figure 9A:
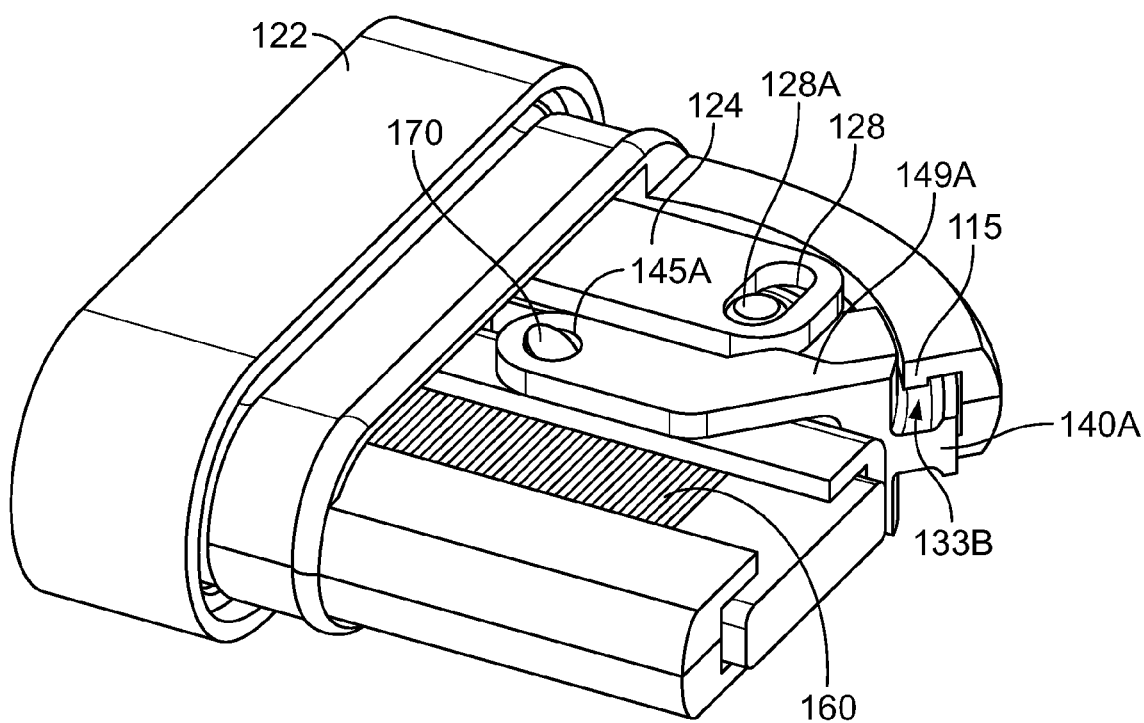
FIG. 9A is an assembled view of certain components of the cartridge shown in FIG. 9.

Turning to FIGS. 9 and 9A, respectively, a cross-sectional view of the assembled cartridge 100, as well as a perspective view of the interior cartridge housing 129 connected to the cover portion 122 of the cartridge 100, is shown. A stack of test strips 160 is shown within recess 133A formed in the first half 132A of interior cartridge housing 129. As shown, each of the plurality of test strips 160 is laid lengthwise and stacked, so that each of the outer edges of test strips 160 is aligned one on top of the other. The length L of the test strips 160 extends along a horizontal plane, whereas the height or thickness T of each test strip of the plurality of test strips 160 extends along a vertical direction. (FIG. 9.) Despite the numerous test strips present in the dispensing assembly 130, each of the plurality of test strips 160 stored within the cartridge 100 can be dispensed one at a time. This arrangement helps to provide for less frequent refilling of the meter with test strips, as required by prior art multistrip meters. It also helps to prevent more than one test strip being dispensed from the dispenser at the same time. Dispensing member 140 and spring loaded block 146 may be arranged within either the first or second halves 132A,132B of the interior cartridge housing 129.

Spring loaded block 146 is positioned below the stack of test strips 160 and biases plurality of test strips 160 toward the top portion of cartridge 100 (near cover portion 122) and toward edge 171 (FIG. 6) of recess 133A. Test strips 160 are also biased in a direction toward finger 147 of dispensing member 140 so that edge 158A contacts an edge 158' (FIG. 9B) of one test strip 160A in the stack of test strips 160. Edge 171 prevents test strips 160 from advancing any further in the vertical direction or toward the cover portion. Support members 127 (FIG. 6,6A) support test strip 160 in recesses 133A, 133A' (not shown).

Flexible dispensing member 140 is shown positioned within channel 133B (FIG. 6) and recess 133A. Arm portion 146 of dispensing member 140 is positioned within the rounded leg portion 139 (FIG. 6) of channel 133B and finger 147 of dispensing member 140 and is positioned within main body 135 of the first half 132A of the interior cartridge 129. As best seen in FIG. 9A, dispensing member 140 is able to move along the channel 133 created from joining channels 133B,133B' of the first and second halves 132A,132B of the interior cartridge housing 129. Edge 112 of arm portion 146 is guided along by the edge 115 (FIG. 9A) of first half 132A and second half 132B, which helps secure dispensing member 140 within channel 133.

Figure 9B:
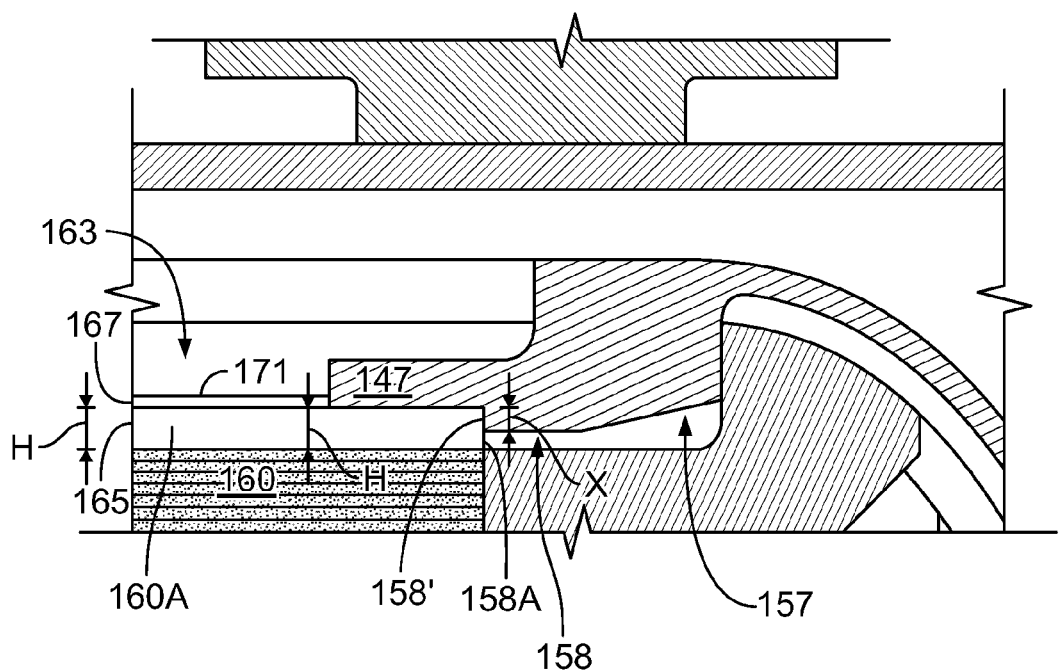
FIG. 9B is an exploded view of a portion of FIG. 9.

With reference to FIG. 9B, an enlarged portion of FIG. 9, finger 147 is positioned so that edge 158A (see also FIG. 7B) of intermediate section 158 is directly adjacent an edge 158' of one of test strips 160A in the stack of multiple test strips 160. For example, as shown, edge 158A of finger 147 has a height X that is slightly less than the height H of a test strip 160A. In one embodiment, the height X of finger 147 can be 0.15 mm less than the height H of test strip 160A. Having the height X of finger 147 less than the height H of test strip 160 ensures that only one test strip will be dispensed from the dispenser at a time. Of course, in other embodiments, the height X of finger 147 could be significantly less or even equal to the height H of test strip 160A.

As also illustrated in FIG. 9B, there is a test strip channel 165 that allows one test strip at a time to travel therein, and a test strip opening 167, where test strip 160A will be dispensed. Finger channel 163 allows finger 147 of dispensing member 140 to travel therethrough when it dispenses a test strip through strip opening 167.

Referring back to FIGS. 4 and 9A, cover portion 122 and dispensing assembly 130 are connected to one another. Connection members 124 extend through elongated apertures 171A,171B (FIG. 4) positioned on top portions of first and second halves 132A,132B of the interior cartridge housing 129 of dispensing assembly 130. Each end of notch 128A of dispensing member 140 extends through respective oblong apertures 128 of connection members 124. In this arrangement, first hinge arm 145A is adjacent connection member 124 and second hinge arm 145B is adjacent connection member 124B.

When the dispensing assembly 130 and cover portion 122 are joined together, block 146A may be positioned below the last test strip in the plurality of test strips 160. Spring 146B may be placed into outer housing 150. As best seen in FIG. 9, in its fully assembled form, cartridge 100 is in an "at rest" position. In this position, spring loaded block 146 biases plurality of test strips 160 toward the top of the interior cartridge housing 129, or the edge 171 of housing. Additionally, at least a portion of hinge main body 151 extends below third leg 139.

Figure 10:
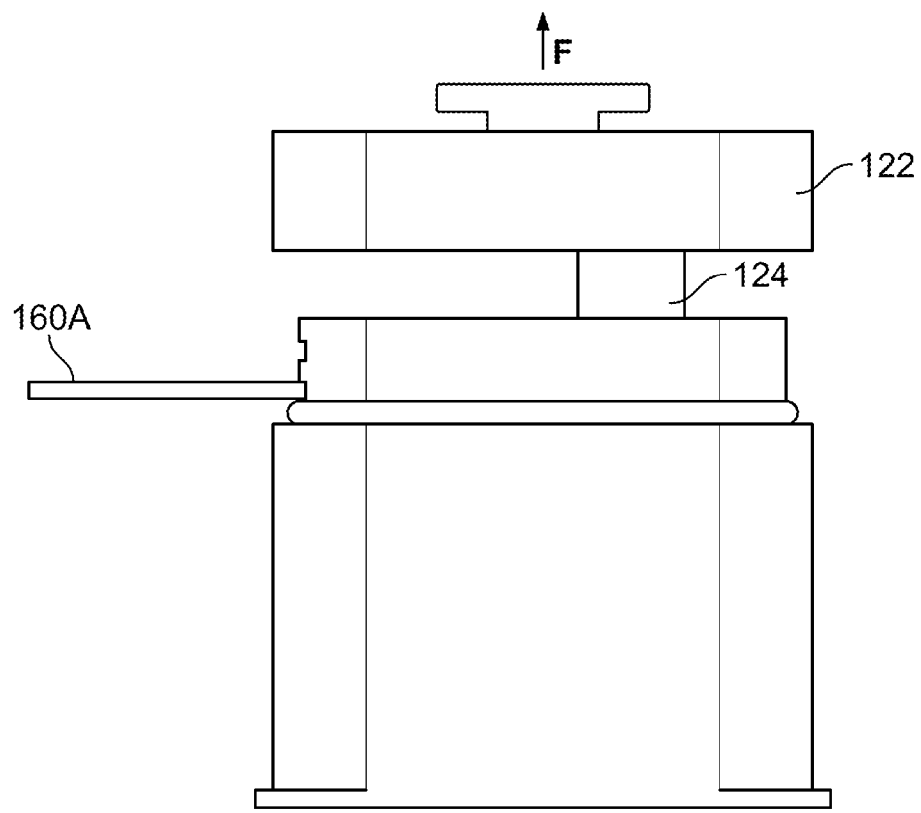
FIG. 10 is a front plan view of the cartridge shown in FIG. 3 in an actuated position.

With reference to FIG. 10, in order to dispense a test strip from the stack of test strips 160, dispensing member 140 must be moved from its "at rest" position to a "dispensing" position. When force F is applied to cover portion 122, connection member 124 also applies a force against notch 128A (FIG. 7A) within the aperture 128 (FIG. 5A), causing notch 128A to move within aperture 128 toward the opposed end of aperture 128. First and second hinge arms 145A, 145B rotate around notch 170, allowing for movement of the dispensing member 140. Dispensing member 140 moves along or within the channel 133 created by the channels 133A,133B of the first and second halves 132A,132B of interior cartridge housing 129 of dispensing assembly 130. Dispensing member 140 therefore moves in an upward or vertical direction, as well as a horizontal direction or parallel to the direction of the test strip. As a result, an upward force F on the cover 122 causes motion in two directions.

Figure 10A:
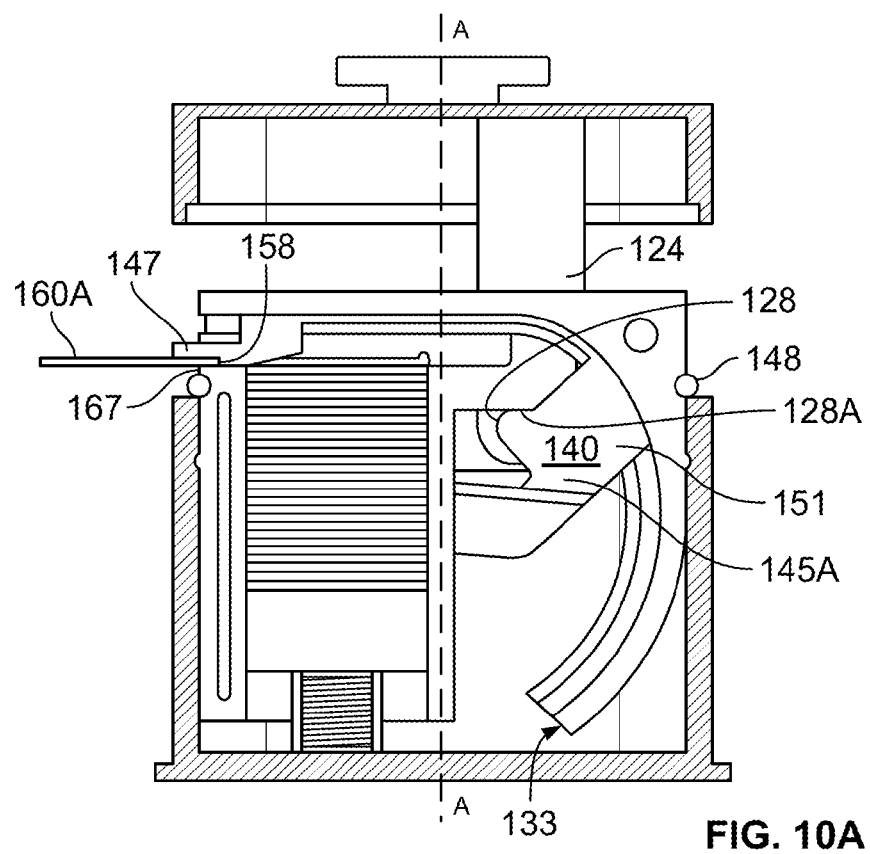
FIG. 10A is a cross-sectional view of FIG. 10.

When dispensing member is moved from its "at rest" position to a "dispensing" position, as edge 158A of finger 147 of dispensing member 140 moves test strip 160A across the top of the stack of test strips 160 and along channel 165 until test strip 160 is pushed out through the strip opening 167. (See also FIG. 9B.) In other words, edge 158 of finger 147 pushes test strip 160A along the test strip channel 165 and out through the test strip opening 167. Test strip 160A therefore displaces test strip 160 so that it is no longer aligned with the remaining test strips. Thus, movement of cover portion 122 along an axis A (FIG. 10A) and away from outer housing 150 causes dispensing member 140 to move between a first or "at rest" position and a second or "dispensing" position. The "at rest" position is when main body 151 of dispensing member 140 is closer to first end 137 of third leg 139 and edge 158A of dispensing member 140 is adjacent a test strip 160A in a stack of test strips 160. The "dispensing" position is one where main body 151 of dispensing member 140 is rotated to move along channel 135B and away from first end 137A of third leg 139, and finger 147 moves along channel 167 and pushes test strip 160A through test strip opening 167.

Figure 11:
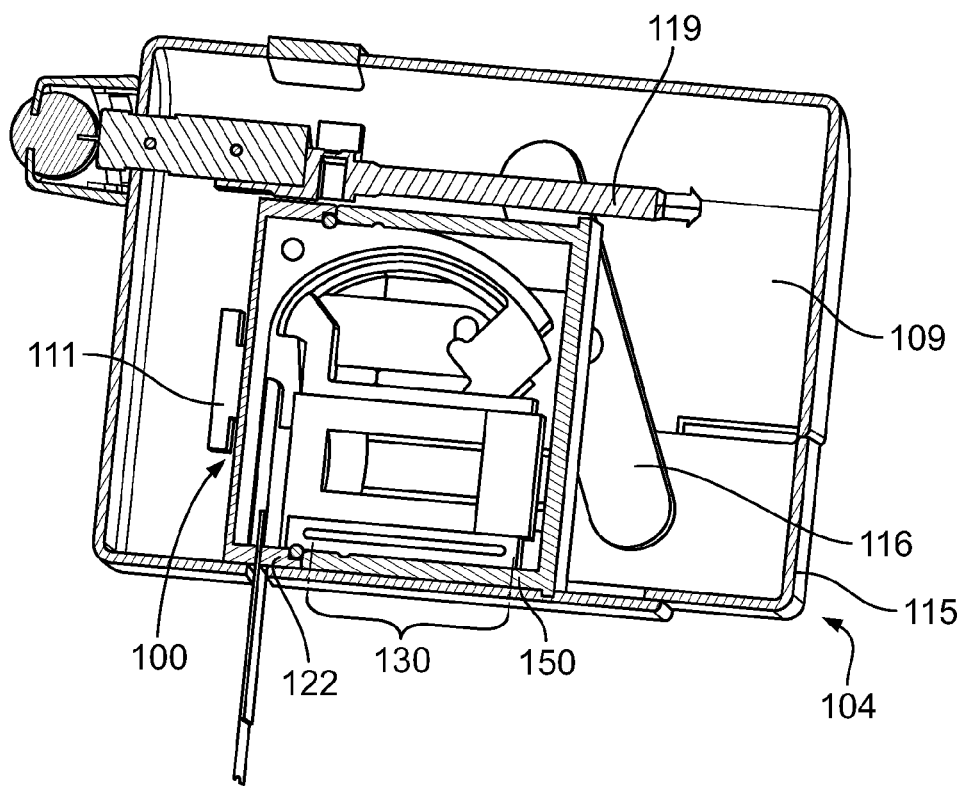
FIG. 11 is an embodiment test meter in accordance with another of the present invention.

Cartridge 100 can be incorporated into a multi-test strip meter to allow for multiple tests to be performed using only the one cartridge 100. In one schematic example, as shown in FIG. 11, cartridge 100 may be placed into the housing of a test meter. Tab 111 of cartridge 100 may be fixed to the housing, such that the outer housing 150 of cartridge 100 is free to move away from cover portion 122. As shown, an actuator 114, including an actuating button 115 and actuating arm 116 may be attached to tab connector 111 of cartridge 100. When a force is applied to actuating button 115, dispensing assembly 130, positioned within the outer housing is actuated, and the outer housing 150 is caused to move away from cover portion 122. This causes dispensing member 140 to move from an "at rest" or first position to its "dispensing" or second position. This causes test strip 160A to be dispensed from the opening in cartridge 100 and meter housing 109. In this example, the test strip 160A has already been dispensed, and the dispensing member 140 has returned from its "dispensing" position near the entrance of the opening in the cartridge to its "at rest" position. It is therefore ready to dispense another test strip 160A. In this example, actuating arm 116 is also connected to a cock release 119, which releases a lancer 121 from its cocked position and ejects lancer 121 from the meter housing. Lancer 121 may be used to prick a finger or other body part to provide a fluid sample onto test strip 160A.

Figure 12:
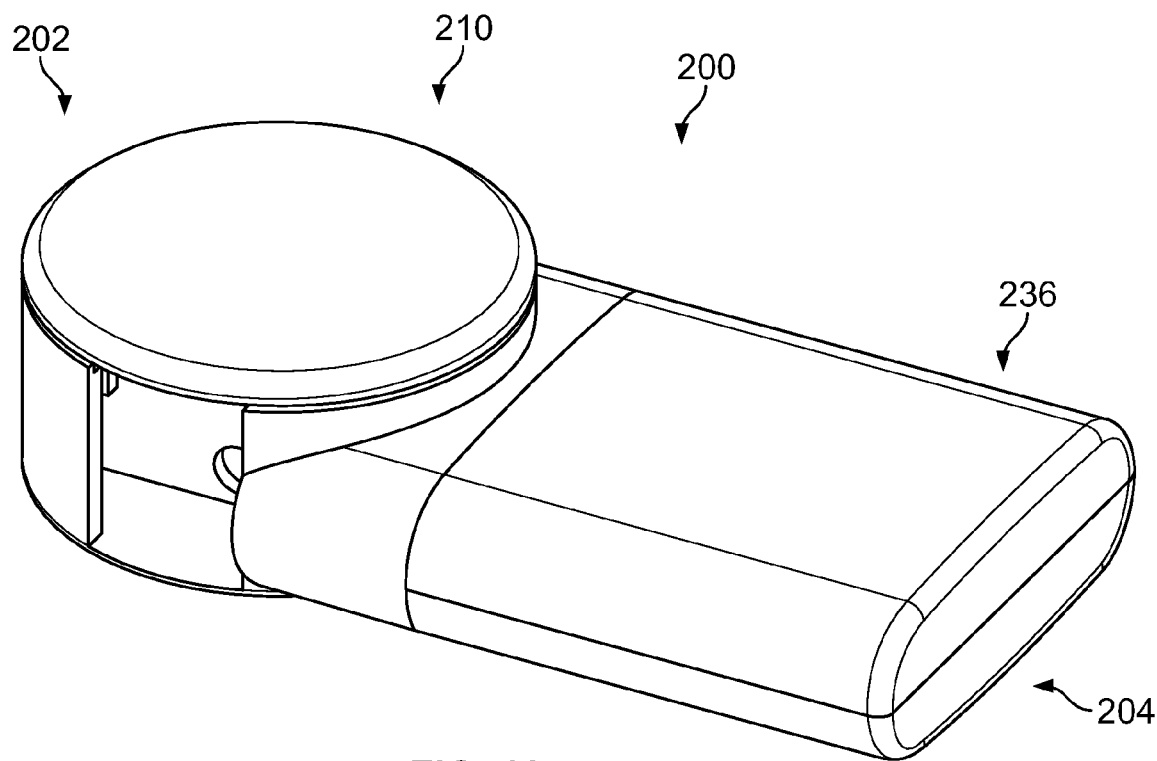
FIG. 12 is a perspective view of a cartridge in accordance with an alternative embodiment.

It is to be appreciated that the foregoing discussion illustrates only one embodiment of the presently disclosed invention and numerous alternative embodiments exist. Another alternative cartridge for use in a multistrip meter is shown in FIG. 12 to FIG. 22A. Turning first to FIG. 12, cartridge 200 is shown in perspective view. Cartridge 200 has two ends. First end 202 is generally rounded and second end 204 is rectangular.

Figure 13:
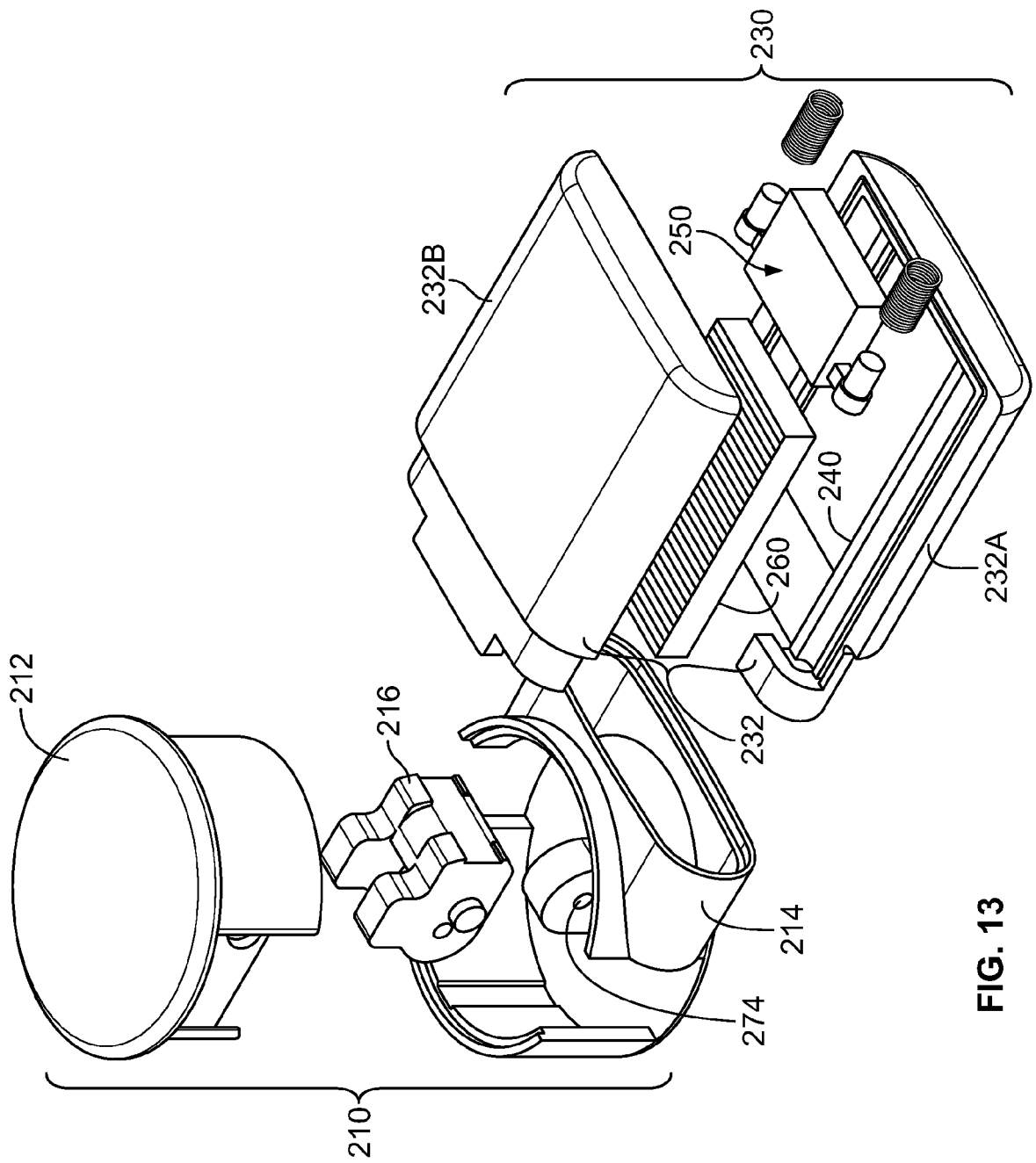
FIG. 13 is an exploded view of the cartridge shown in FIG. 12.

With reference to FIG. 13, an exploded view of FIG. 12 is shown. In one embodiment, cartridge 200 is comprised of two major components: a dispensing assembly 210 and a test strip storage unit 230 removably connected to the dispensing assembly 210. Each of these components will be discussed in greater detail herein. Storage unit 230 stores a plurality of test strips 260. Storage unit 230 is generally comprised of an outer storage housing 232 and a spring loaded block 250.

Figure 14:
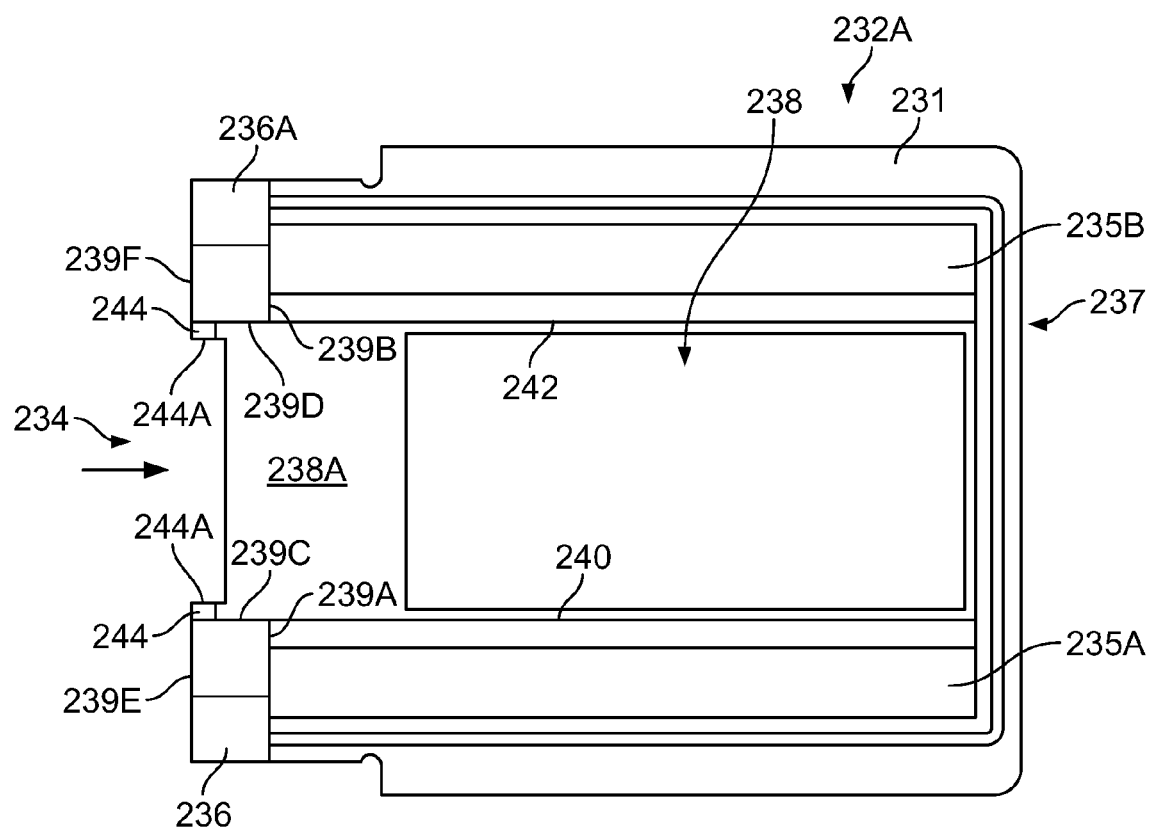
FIGS. 14 and 14A are respective top and bottom plan views of housing components shown in FIG. 13.

Outer storage housing 232 is further comprised of a first half 232A and a second half 232B that are joined together. With reference to FIG. 14, first half 232A has a generally rectangular shape with rounded edges, a first open end 234 and a second closed end 237. Raised channels 235A and 235B extend between first and second ends 234,237 of first half 232A. Raised channels 235A,235B form respective raised edges 240,242 that define an interior recess 238 for receiving test strips 260 and spring loaded block 250. At first end 234, channel 235A terminates at first stop 236 and second channel 235B terminates at a second stop 236A. First stop 236 includes an interior channel edge 239A, an outer edge 239E, and a lateral edge 239C extending between interior channel edge 239A and outer edge 239E. Similarly, second stop 236A includes interior channel edge 239B, an opposed outer edge 239, and a lateral edge 239D that extends between channel edge 239B and opposed outer edge 239. There is also a dispensing ledge 244 that is recessed below interior surface edge 238A. As a result, an interior edge 244A extends between interior surface 238 and dispensing ledge 244.

Figure 14A:
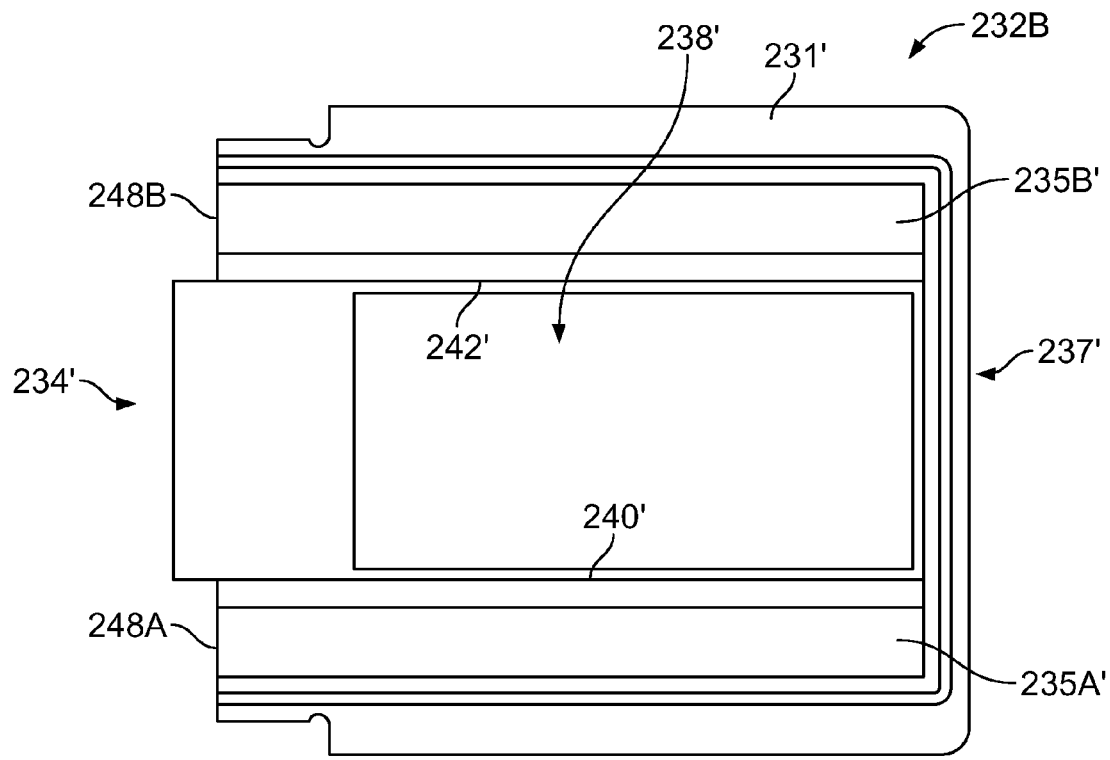

Turning now to FIG. 14A, second half 232B is complementary to first half 232A. Second half 232A includes a first end 234' and second end 237'. Additionally, first and second channels 235A' and 235B' also extend between first and second ends 234', 237' and have respective raised edges 240', 242'. Interior recess 238' is defined by raised edges 240',242' and includes the space between raised edges 240' and 242'.

Dessicant (not shown) may be provided within the first and second halves 232A,232B to ensure test strips stored within the test strip storage unit are not contaminated and that when sealed, a moisture-impervious environment for storing the plurality of test strips 260. When first half 232A and second half 232B of storage unit 230 are joined together, second ends 237,237' will be aligned. At first ends, edge 239C of second half 232B will abut edge 239B of second stop 238 of first half 232A. Similarly, second edge 239D will abut edge 239A of first stop 236 of first half 232A. Additionally, 239D of second half 232B will be respectively joined to raised edges 239B, 239A.

Figure 15:
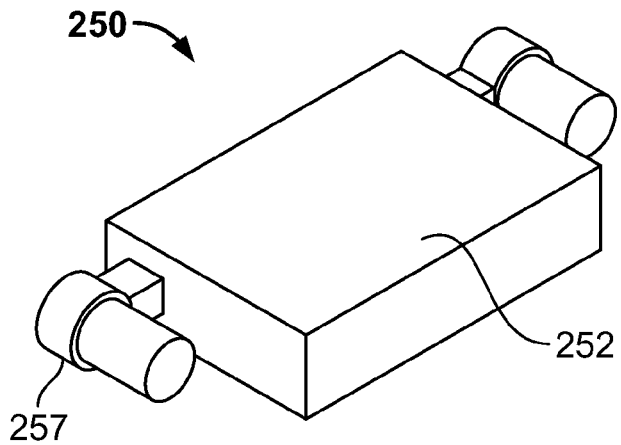
FIG. 15 is a perspective view of the block component of the cartridge shown in FIG. 13.
Figure 15A:
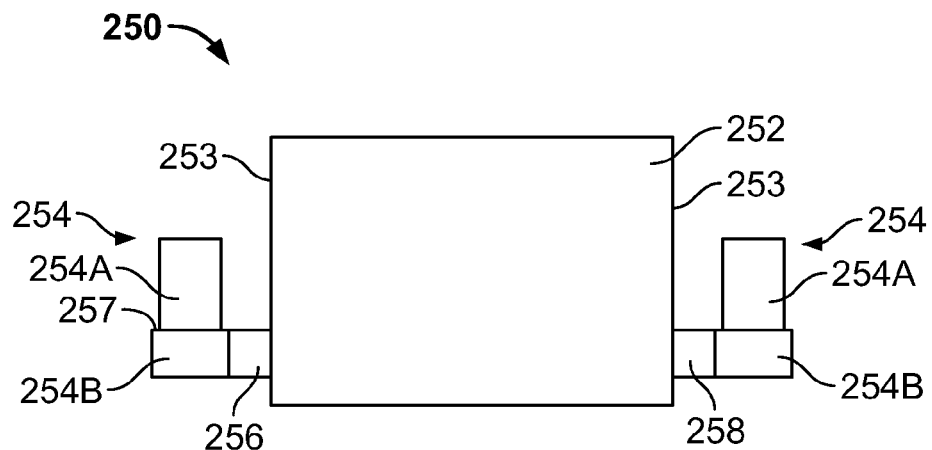
FIG. 15A is a front plan view of the component shown in FIG. 15.
Figure 15B:
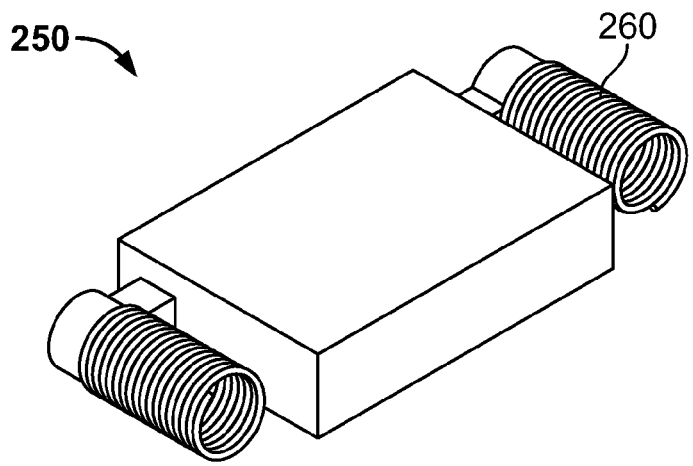
FIG. 15B is a perspective view of the block component with a biasing member thereon.

Spring loaded block 250 is best shown in FIGS. 15, 15A, and 15B. As shown, spring loaded block 250 is comprised of a generally rectangular main body 252. First arm 254 and second arm 256 extend from connectors 256 that, in turn, extend from opposed edges 253 of main body 252. In this embodiment, first and second arms 254,256 are circular and comprised of a first portion 254A that has a smaller diameter than the diameter of second portion 254B. A ledge 257 is formed between first and second portions 254A,254B. As shown in FIG. 15B, springs 261 can be provided over first portion 254A and rest on ledge 257.

Figure 16:
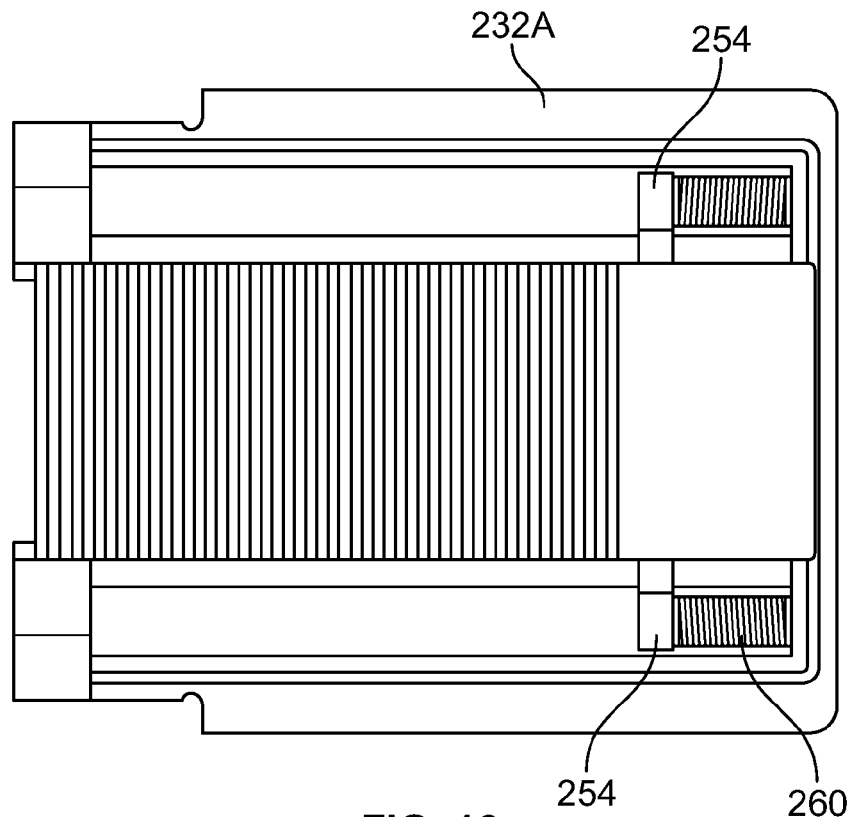
FIG. 16 is a top plan view of the component of the cartridge component shown in FIG. 15.
Figure 16A:
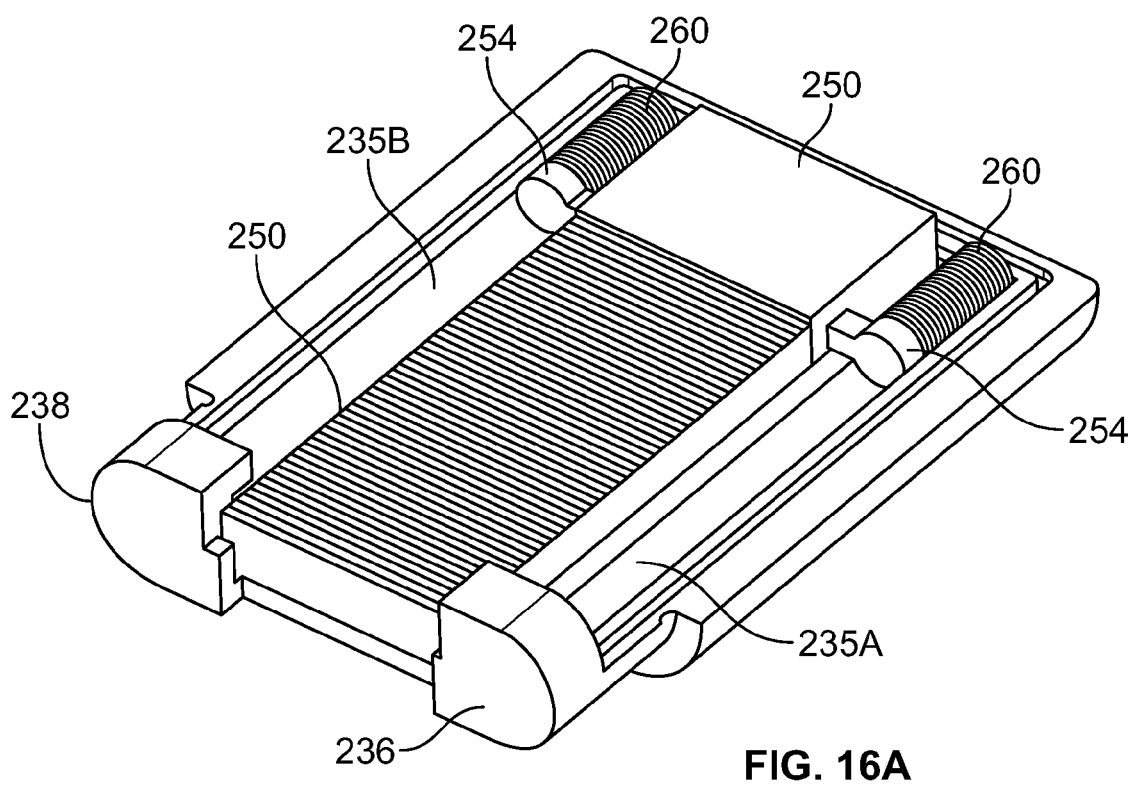
FIG. 16A is a perspective view of FIG. 16.

Turning now to FIGS. 16 and 16A, first half 232A is shown with test strips 260 and spring loaded block 250 therein. As shown, arms 254 are positioned within the first and second channels 235A,235B so that they can freely move within the channel as test strips 260 are dispensed from storage unit 230. Second half 232B can be joined to first half 232A along joining surface 231 (FIG. 14) of first half 232A and joining surface 231' of second half 232B, using known methods.

Figure 17:
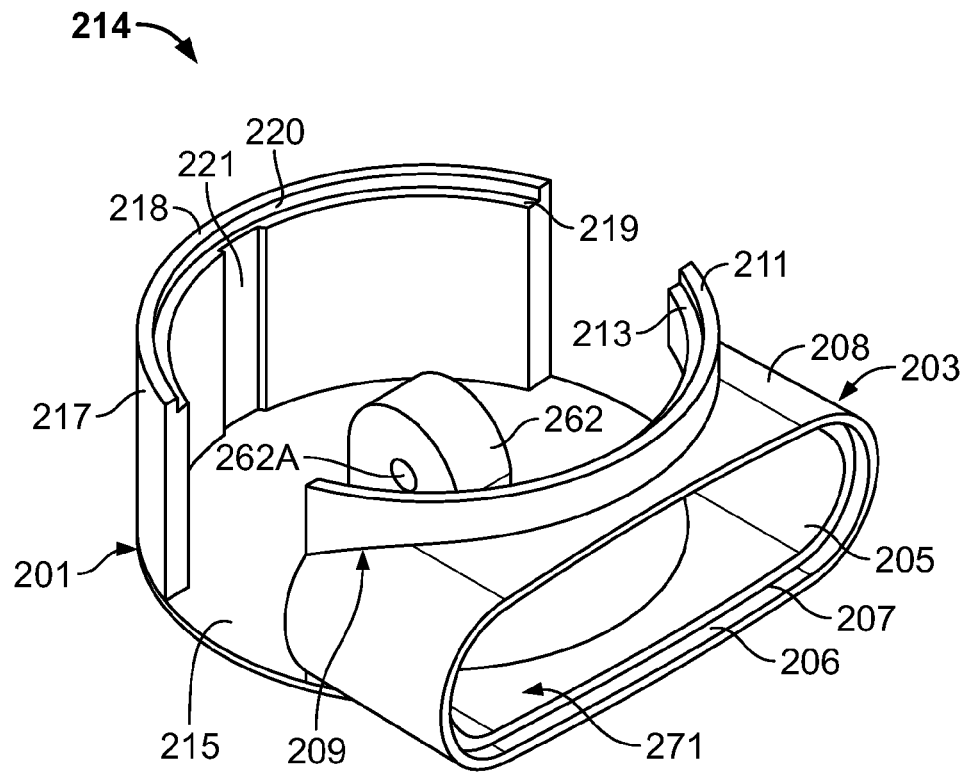
FIG. 17 is a perspective view of the dispensing housing of FIG. 12.
Figure 17A:
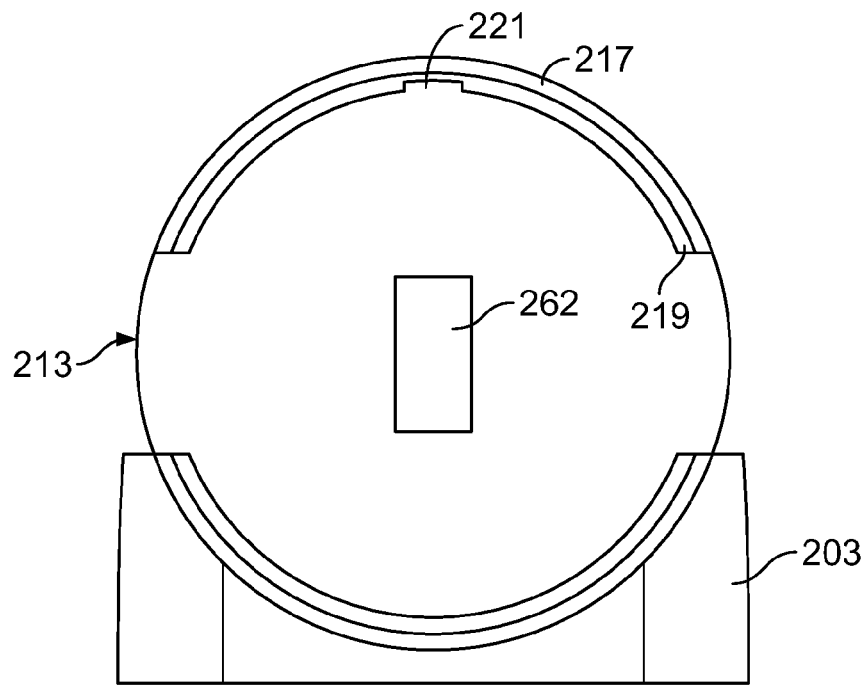
FIG. 17A is a top plan view of the dispensing housing.

Referring back to FIG. 13, in this embodiment, dispensing assembly 210 is comprised of three primary components: cover 212, dispensing housing 214, and dispensing member 216. With reference now to FIGS. 17 and 17A, dispensing housing 214 is shown having a main body 201 that has a circular base 215. Semi-circular first wall 217 extends around a portion of base 215 and has an outer top surface 218 and an interior top surface 219. Edge 220 (FIG. 17) extends between outer top surface 218 and interior top surface 219, such that interior top surface 219 is spaced away from outer top surface 218 and forms a ledge. Channel 221 extends from interior top surface 219 to base 215. Connector 203 extends along a portion of base 215 that is directly opposed to the portion of the base 215 from which the semi-circular wall extends. Connector 203 has an oval-shaped opening with a surface 205 that extends continuously from base 215. Second surface 206 is positioned at the mouth of the opening to the connector and spaced away from first surface 205 so that a vertically-extending edge 207 extends between first and second surfaces 205, 206. A second wall 209 extends upwardly from top surface 208 of connector 203.

Figure 17B:
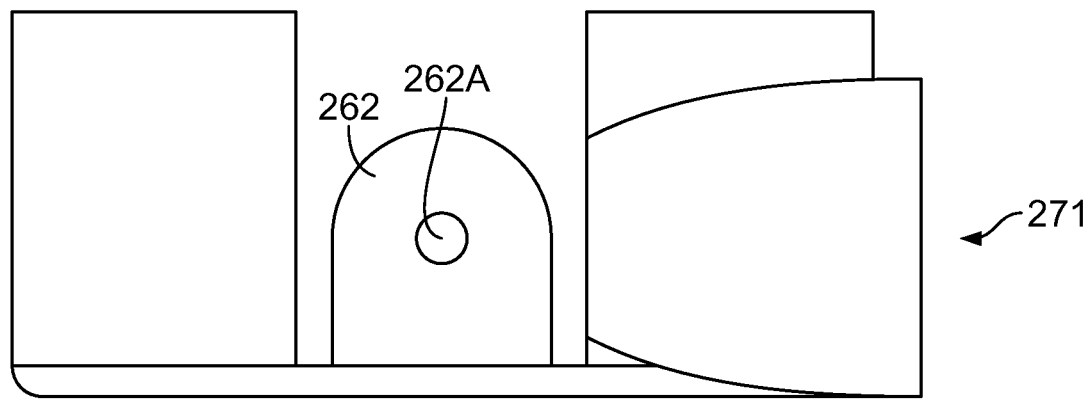
FIG. 17B is a side perspective view of the component shown in FIG. 17.
Figure 17C:
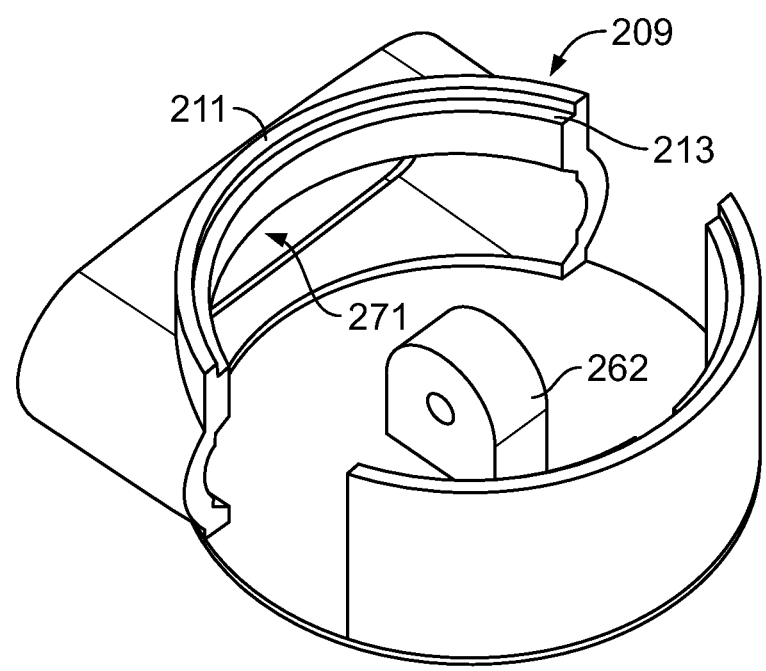
FIG. 17C is a rear perspective view of the component shown in FIG. 17.

As best seen in FIG. 17C, a rear perspective view, wall 209 is rounded and mimics the shape or contour of circular base 215. Wall 209 also includes a first outer surface 211 and a first inner surface 213 spaced away from first outer surface 211. Additionally, wall 209 further includes a channel facing the interior of dispensing housing 214 that extends along the portion of wall 209 facing first wall 217.

With reference to FIG. 17B, post 262 is positioned within dispensing housing 214 that extends away from base 215 of main body 201. Post 262 includes an opening extending there through.

Figure 18:
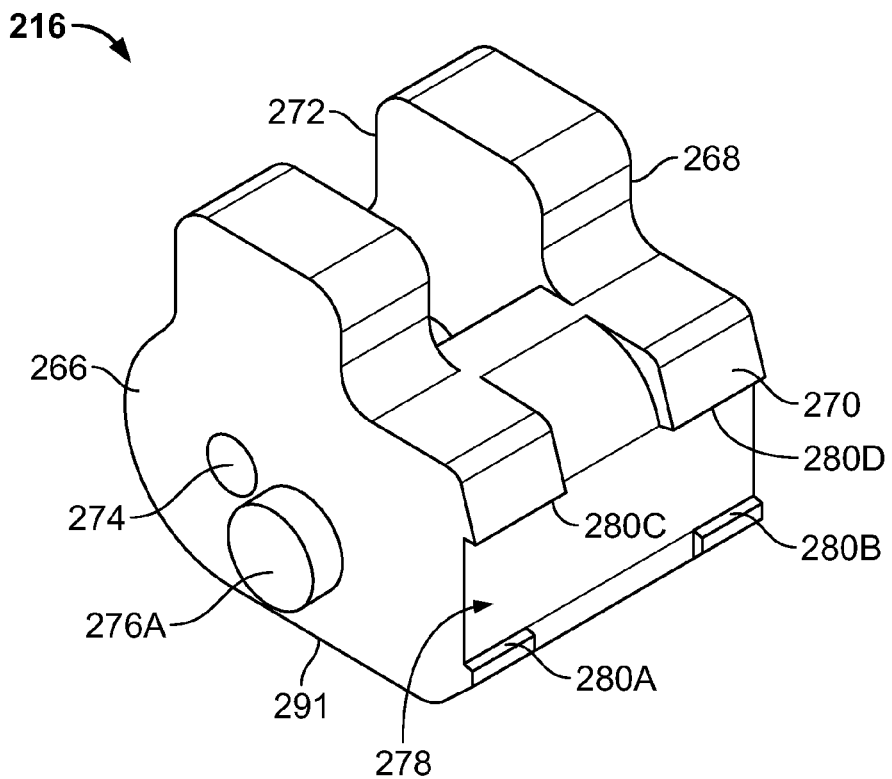
FIG. 18 is a perspective view of the dispensing member shown in FIG. 13.
Figure 18A:
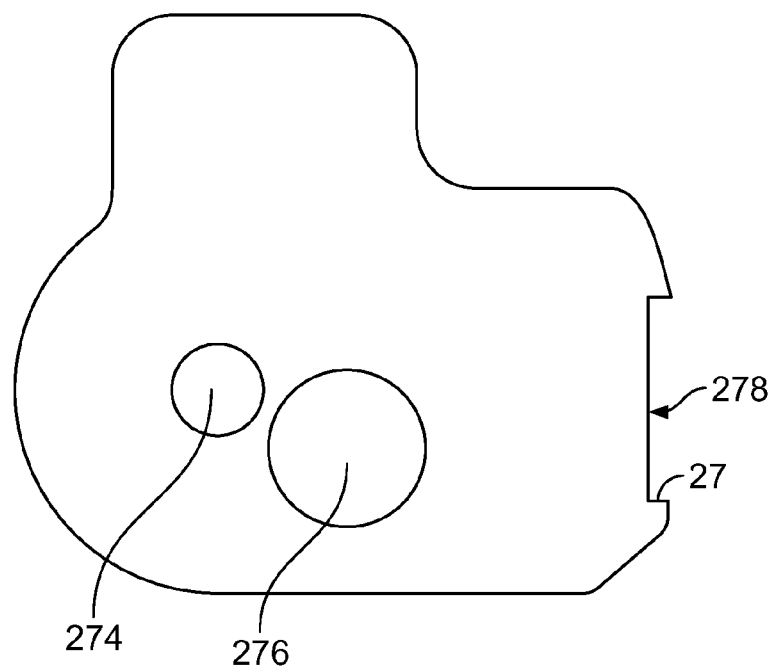
FIG. 18A is a side plan view of the dispensing member shown in FIG. 13.

Turning now to FIGS. 18 and 18A, there is shown a dispensing member 216. Dispensing member 216 includes a front face 266, a rear face 268, a first lateral face 270, and a second lateral face 272. Opening 274 extends between front and rear faces 266,268, and front posts 276A extend away from front face 266, and a rear post 276B (not shown) extends away from rear surface 268. First lateral face 270 includes a recessed portion 278. Edges 280A,280B,280C, and 280D form supports that will be used to hold a test strip in place.

Figure 19:
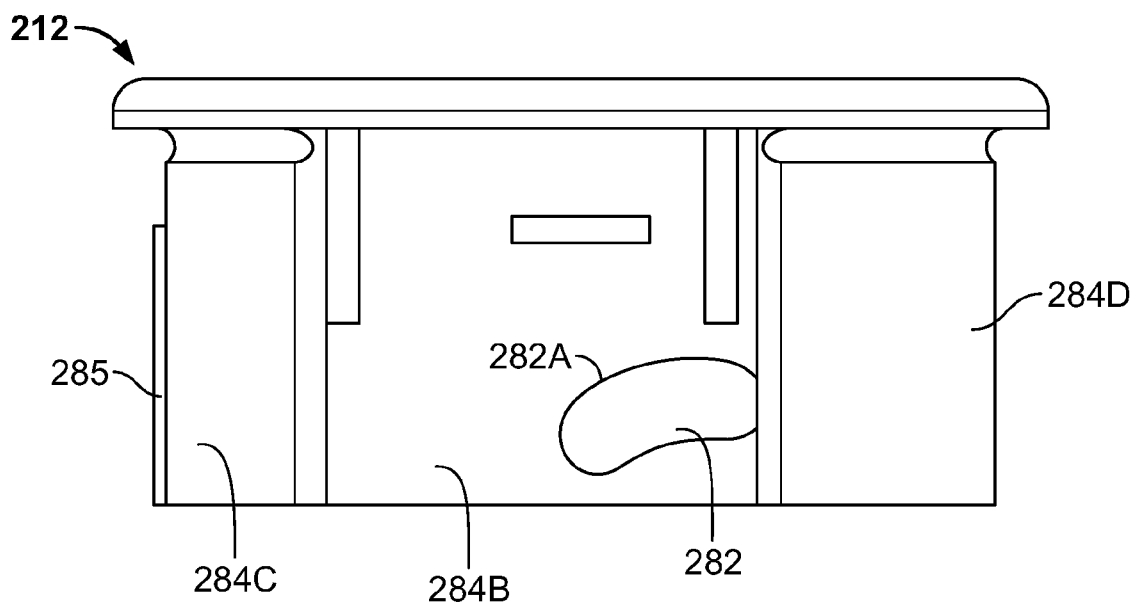
FIG. 19 is a front plan view of the cover of the cartridge shown in FIG. 13.
Figure 19A:
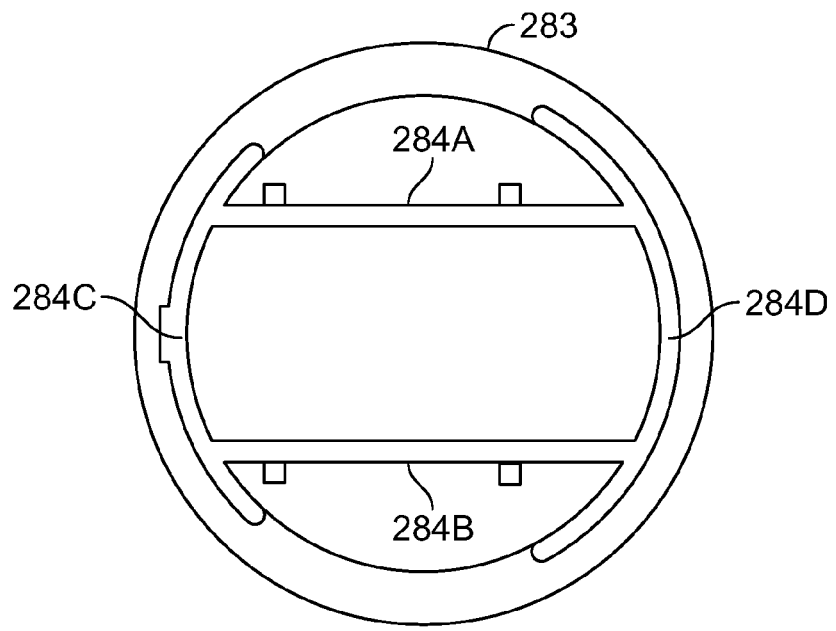
FIG. 19A is a bottom plan view of the cover shown in FIG. 19.
Figure 19B:
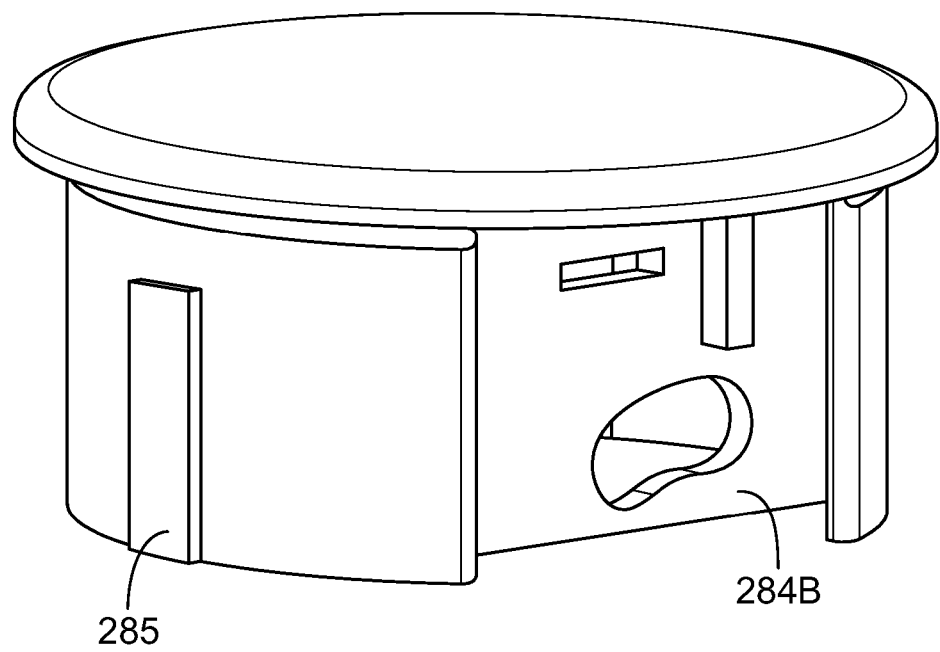
FIG. 19B is a perspective view of the cover shown in FIG. 19.
Figure 19C:
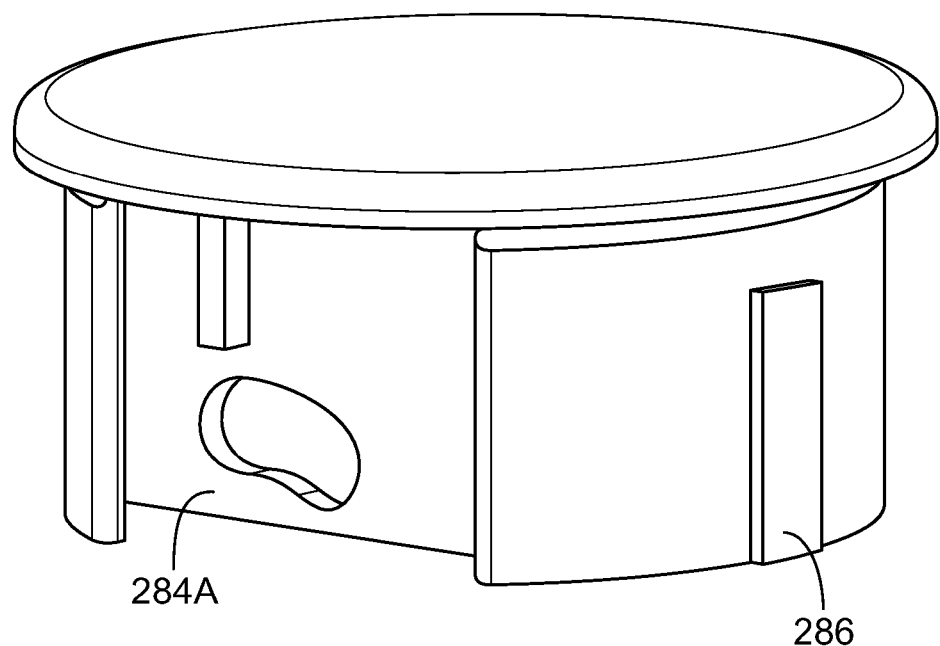
FIG. 19C is a front perspective view of the cover shown in FIG. 19.

With reference to FIG. 19, cover portion 212 is further explained. As shown in the front plan view, cover portion 212 is round in shape and constructed and arranged to fit into the main body 201 of dispensing housing 214. As best illustrated in FIGS. 19A, 19B, and 19C, walls 284A-284D extend from the circular top portion 283. Walls 284C,284D are rounded and follow the shape of circular top portion 283. Walls 284A, 284B are horizontal lines that intersect both walls 284C, 284D. A kidney shaped recess 282 extends through each of the walls 284A,284B and has a peripheral edge 282A. Positioning tab 285 is positioned on an outer surface of wall 284A.

Figure 20:
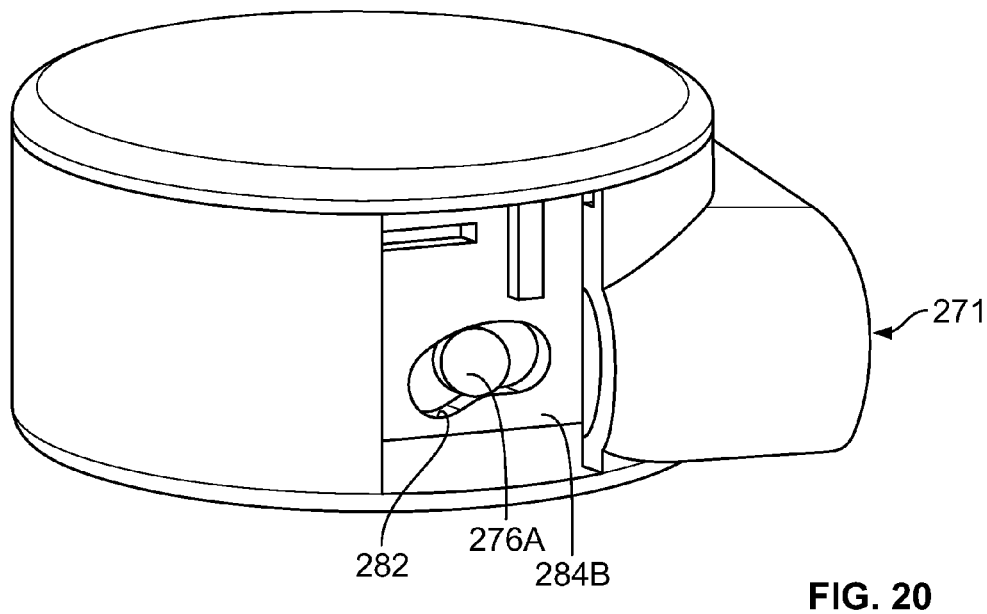
FIG. 20 is a perspective view of the cover within the dispensing housing, in accordance with one embodiment.
Figure 20A:
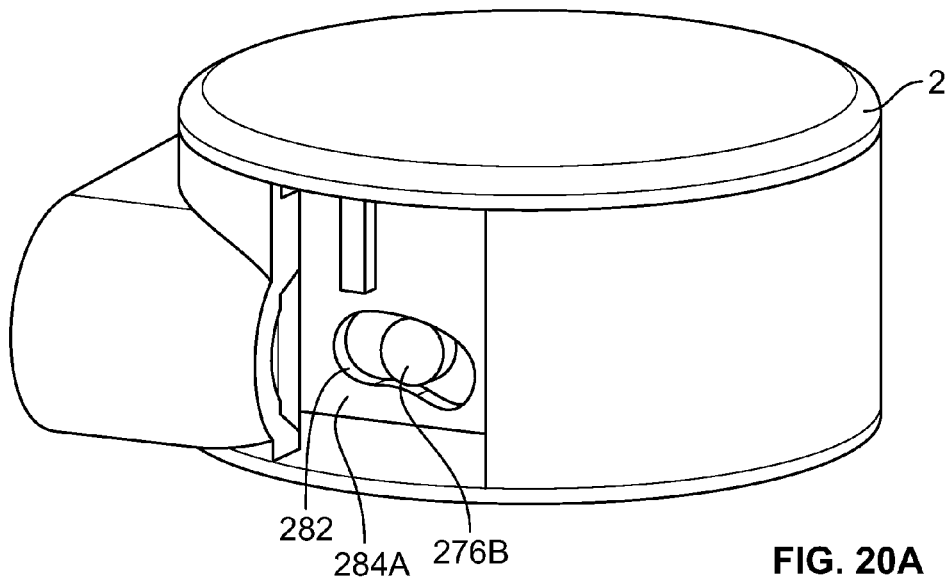
FIG. 20A is a rear perspective view of FIG. 20.

With reference back to FIGS. 13, 20, 20A, in order to assemble dispensing assembly 210, dispensing member 216 is secured to post 262 (FIG. 17,17A,17B) of dispensing assembly housing 214. Opening 274 in dispensing member 216 is aligned with opening 262A in post 262. A pin (not shown) may then be provided through the openings 262A, 274 and secured within the openings 262A,274. This will secure dispensing member 216 to post 262, while allowing dispensing member 216 to rotate about post 262. In the "at rest" position, first lateral face 270 of dispensing member 216 faces the opening 271 (FIG. 17) in housing 214. Cover portion 212 may then be provided within the housing 214. Cover portion 212 must be oriented so that tabs 285 (FIG. 19,19B) on cover portion 212 are aligned with channel 221 on the dispensing housing. With reference to FIG. 20, kidney shaped openings 282 in cover portion 212 can be provided over posts 276A,276B so that posts 276A,276B are secured within kidney shaped openings 282. This allows for posts 276A,276B of cover portion 212 to move within kidney shaped openings 282. With the kidney shaped openings 282 in communication with posts 276A,276B, a force F applied to cover portion 212 in an upward direction will cause dispensing member 216 to be rotated in an upward direction, so that front face 270 is facing cover portion 212.

Figure 21:
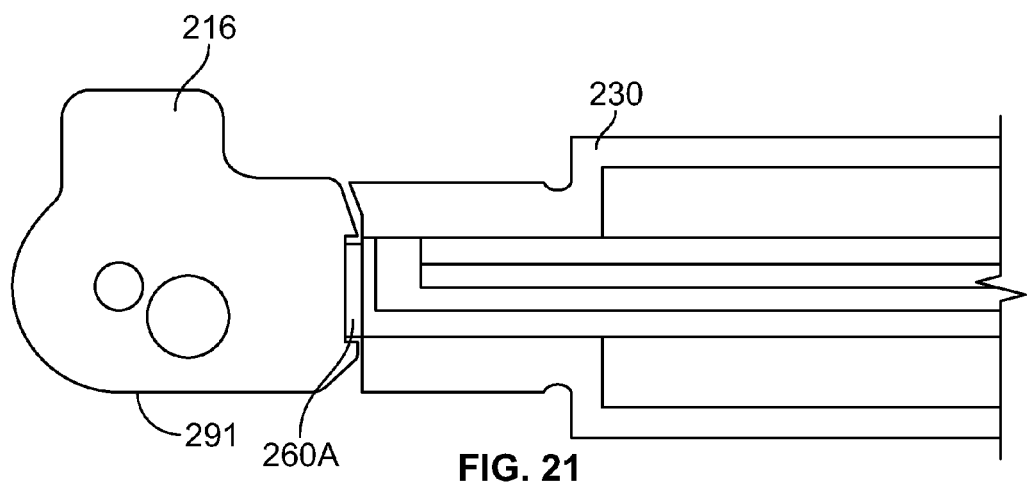
FIG. 21 is a cross-sectional view of portions of the cartridge shown in FIG. 12.
Figure 21A:
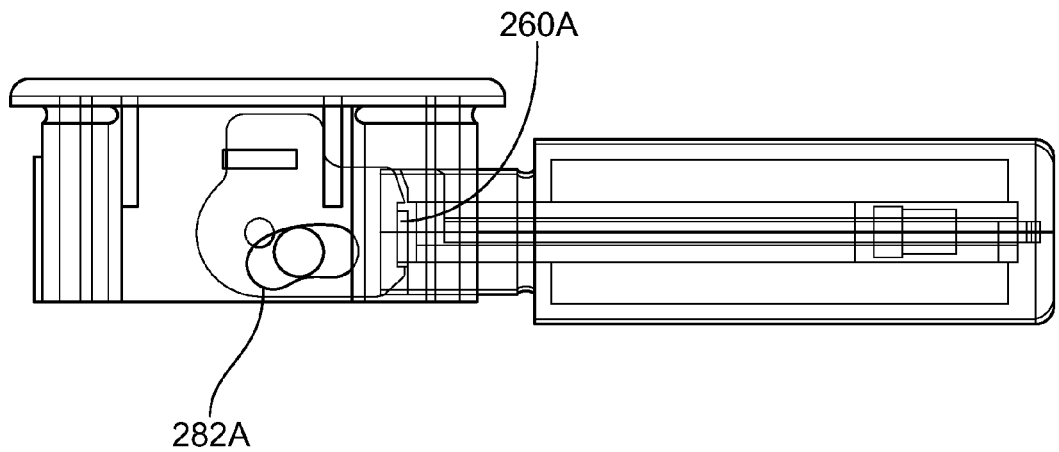
FIG. 21A is a cross-sectional view of the entire cartridge shown in FIG. 12.

To operate test strip dispenser assembly 210, storage unit 230 may be placed into opening 271 of the connector 203. Turning now to FIGS. 21 and 21A, there is respectively shown a dispensing member 216 and storage unit 230 in cross-section, as well as a cross-section of the entire cartridge 200 in an "at rest" position. When storage unit 230 is joined with dispensing member 216, storage unit 230 abuts dispensing member 216. In this "at rest" position, test strip 260A is positioned at the front of the plurality of test strips 260 stored in test strip storage unit 230. As shown, test strip 260 sits within recess 278 created by edges 227. (See also FIG. 18.) The dispensing member 216 is designed so that only one single test strip can fit within the dispensing member 216, making only one test strip available for distribution at a time.

Figure 22:
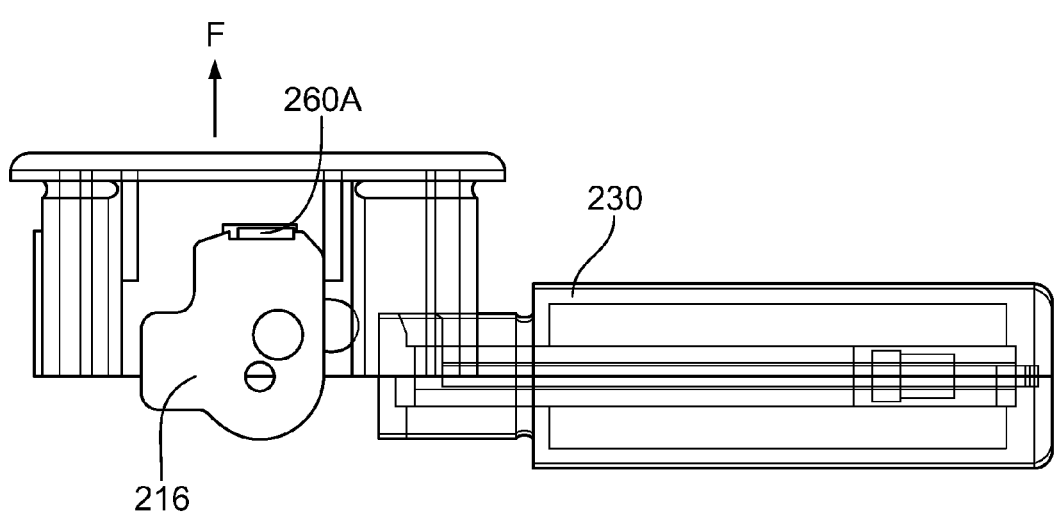
FIG. 22 is a cross-sectional view of portions of the cartridge shown in FIG. 12, when the cartridge is in an open position.
Figure 22A:
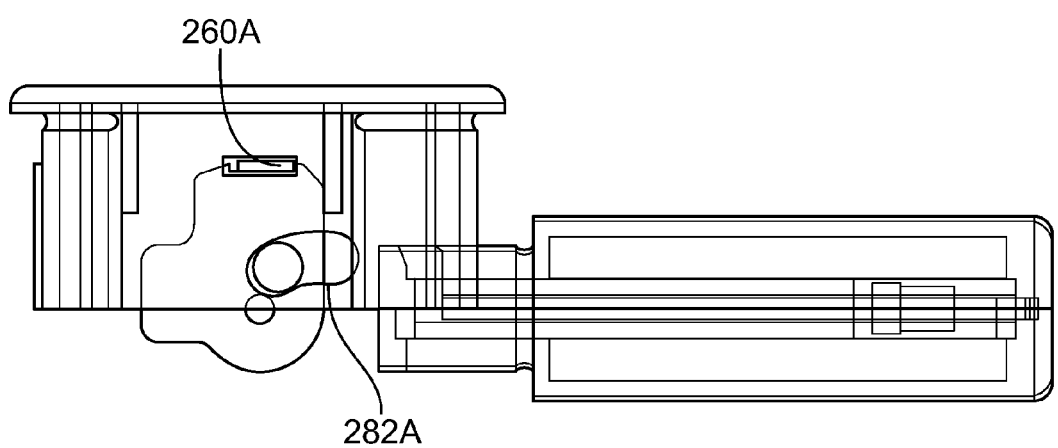
FIG. 22A is a cross-sectional view of the entire cartridge shown in FIG. 12, when the cartridge is in an open position.

When a force F is applied to cover portion 212, posts 276A,276B (FIG. 18) are caused to move by the force applied to cover portion 212, which causes edges 282A of kidney shaped openings 282 to catch posts 276A,276B and allow movement of posts 276A,276B along the kidney shaped openings 282. Dispensing member 216 is caused to rotate about pin (not shown) extending through the dispensing member 216, so that the test strip 260A moves from its "at rest" position into a dispensed position. As best seen in FIG. 22, in this position, test strip 260A is facing cover portion 212 and the base portion of dispensing member 216 covers the opening in storage unit 230, so as to prevent further test strips 260 in the storage unit 230 from falling out. The test strip may then be excised from the cartridge using any conventional means known in the art. For example, there may be an additional opening provided in the cover portion 212 to allow for removal of the test strip. Alternatively, test strip 260A may be pushed out of an opening in the cover portion 212.

When the cover portion 212 is released, front face 270 of dispensing member again faces test strip storage unit 230, and receives the next test strip for distribution.

It is to be appreciated that in any of the previously discussed embodiments, alternative biasing members or means may be used in place of a resilient member, such as a spring, to bias the test strips 160,260 toward the top or edge 171 of cartridge 100 or ledge 244 of the storage unit 230. In alternative embodiments, the biasing member may include a first magnet disposed on the interior bottom surface of the outer housing 150 of cartridge 100 or outer housing 232 of test strip storage unit 230 and a second repulsively disposed magnet attached to the stack of test strips 160,260. The stack of test strips 160,260 is biased forward via electromagnetic forces that cause the first magnet and the second magnet to repulse (i.e., push away from) each other. In another alternative embodiment, the magnets comprise opposing ferromagnets as opposed to electromagnets. Alternatively, a combination of electromagnets and ferromagnets may be used.

In still other alternative embodiments, the biasing member may comprise a pneumatic system wherein a compressed gas is used to bias the stack of test strips 160,260 toward the top or edge 171 of cartridge 100 or ledge 244 of the storage unit 230. According to one alternative embodiment, the stack of test strips 160,260 is disposed on the top side of a piston in a piston-cylinder arrangement, wherein the cartridge 100,200 serves as the cylinder. A compressed gas disposed in the cylinder, beneath the piston, biases the stack of test strips 160,260 towards the top of cartridge 100 or storage unit 230.

The following numbered paragraphs describe features in accordance with embodiments of the disclosure:

1. A test meter for analyzing a body fluid sample applied to a test strip, the test meter comprising:
 an outer housing having an opening;
 an actuator positioned adjacent the outer housing; and
 a cartridge for dispensing test strips positioned adjacent the outer housing, the cartridge further comprising:
 a dispensing member connected to the actuator;
 a plurality of stacked test strips biased toward the dispensing member; and
 a cartridge outer housing adjacent at least a portion of the dispensing member,
 wherein each time the actuator is actuated, the dispensing member is rotated to cause movement of one test strip from the plurality of stacked test strips through the opening, and another test strip is biased toward the dispensing member.

2. The meter of paragraph 1, wherein the dispensing member is a flexible arm having a first end a second end, wherein when the actuator is actuated, dispensing member moves one test strip across the top of the stack of strips through the opening.

3. The meter of paragraph 2, wherein the dispensing member has a first end and a second end, the first end being a free end contacting the test strip, and the second end being a fixed end, the free end rotating about the fixed end when the actuator is actuated.

4. The meter of paragraph 1, wherein the dispensing member is a rotatable block having a recess for receiving one test strip from the plurality of stacked test strips, and wherein when the actuator is actuated, the block rotates and moves the test strip received within the recess away from the stack of test strips.

5. The meter of paragraph 1, wherein the dispensing member and plurality of test strips are positioned within the outer housing.

6. The meter of paragraph 1, wherein only the dispensing member is positioned within the outer housing, and the cartridge is connected to the outer housing.

7. The test meter of paragraph 1, wherein the test meter is able to analyze the fluid sample while the dispensed test strip remains in the opening.

8. The test meter of paragraph 1, wherein the cartridge further comprises an interior cartridge housing joined with the outer housing, and a cover having a connecting portion engaged with the dispensing member, the cover causing the dispensing member to move.

9. The meter of paragraph 1, wherein the cartridge further comprises a channel for receiving the dispensing member and providing a pathway that allows the dispensing member to move between a first position and a second dispensing position within the channel.

10. The meter of paragraph 1, wherein the cartridge further comprises:
 a cover removably joined together with the outer casing; and
 an interior cartridge housing for housing the dispensing member, the interior cartridge housing further including a test strip storage area for storing the plurality of stacked test strips therein, each of the test strips having edges aligned with one another.

11. The test meter of paragraph 10, wherein each of the stacked test strips have an outer edge, and wherein each of the outer edges are aligned with one another within the test strip storage area.

12. The meter of paragraph 10, further comprising a seal extending between the interior cartridge housing and the outer housing.

13. A method for testing a fluid sample deposited on a test strip, the method comprising:
 actuating a dispensing member contained in a test meter to move from a stationary position to a dispensing position and to cause one test strip in contact with the dispensing member and stored within a stack of test strips in the test meter to move toward an opening in the test meter, at least one edge of the one test strip being exposed and an opposed edge of the test strip remaining within the opening when the test strip is moved toward the opening;
 providing the fluid sample on the exposed portion of the test strip;
 analyzing the fluid sample while the opposed edge of the one test strip remains; and
 biasing another test strip toward the dispensing member.

14. The method of paragraph 13, wherein the dispensing member comprises a movable arm having a fixed end and a free end, the free end contacting the one test strip.

15. The method of paragraph 14, wherein the dispensing member rotates about a fixed point when it moves the test strip from a first position to a second position.

16. The method of paragraph 13, wherein the dispensing member is a movable block capable of moving the test strip from a first position to a second position.

17. The method of paragraph 14, wherein the block has a recess for receiving one strip.

18. The method of paragraph 13, wherein the cartridge further comprises a cover connected to the actuator and the dispensing member further includes a cover, the dispensing member having a first end and a second dispensing end, the dispensing member being a flexible arm capable of moving between a first position and a second position each time the actuator is actuated.

19. A cartridge for use in a test meter, the cartridge comprising:
 an outer casing;
 a cover removably joined together with the outer casing;
 a dispensing assembly seated within the outer casing, the dispensing assembly further comprising:
 a test strip storage area for storing a plurality of stacked test strips therein, each of the test strips having edges aligned with one another; and a dispensing member movably connected to the cover and contacting a single test strip of the plurality of test strips, and a biasing member for moving the plurality of stacked strips toward the dispensing member, wherein the dispensing member rotates between a first rest position to a second dispensing position, and wherein the dispensing member moves the one test strip through the opening when the cover is moved away from the dispensing assembly.

20. The cartridge of paragraph 19, wherein the dispensing member is an elongated member having a first free end and a second fixed end, the dispensing member moving about the second end.

It will be appreciated that various features set forth in the embodiments discussed herein can be combined in different ways then presented herein. It will also be appreciated that the features described in connection with individual embodiments may be shared with other embodiments discussed herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A test meter for analyzing a body fluid sample applied to a test strip, the test meter comprising:
    an outer housing having an opening;
    an actuator positioned adjacent the outer housing;
    a dispensing member movably connected to the actuator, the dispensing member having a first end and a second end, the first end being a free end and the second end being a fixed end, the dispensing member configured to rotate about the fixed end; and
    a cartridge for storing a plurality of stacked test strips for distribution through the opening, the cartridge having a linear channel configured to permit movement of the dispensing member there through, the cartridge comprising a covering element hingedly connected to the dispensing member and configured to move the dispensing member when the covering element moves between a first position and a second actuated position, the covering element engaged with the actuator and moving from the first position to the second actuated position when the actuator is actuated;
    wherein the plurality of stacked test strips is biased toward the dispensing member, and
    wherein each time the actuator is actuated, the dispensing member is rotated about the fixed end, and the free end of the dispensing member moves along the linear channel to move one test strip from the plurality of stacked test strips through the opening and another test strip from the plurality of stacked test strips is biased toward the dispensing member.

2. The test meter of claim 1, wherein the dispensing member is a flexible arm, and wherein when the actuator is actuated, the dispensing member moves one test strip across a top of the plurality of stacked strips.

3. The test meter of claim 1, wherein the dispensing member and plurality of test strips are positioned within the outer housing.

4. The test meter of claim 1, wherein only the dispensing member is positioned within the outer housing, and the cartridge is connected to the outer housing.

5. The test meter of claim 1, wherein the test meter is able to analyze the fluid sample while the dispensed test strip remains within the opening.

6. The test meter of claim 1, wherein the cartridge further comprises:
    an interior cartridge housing joined with the outer housing.

7. The test meter of claim 1, wherein the linear channel is constructed and arranged to provide a pathway that allows the dispensing member to move between a stationary position and a dispensing position within the channel, wherein the dispensing member is closer to the opening in the dispensing position than in the stationary position.

8. The meter of claim 1, wherein the cartridge further comprises:
    an interior cartridge housing for housing the dispensing member, the interior cartridge housing including a test strip storage area for storing the plurality of stacked test strips therein, each of the test strips having edges aligned with one another.

9. The test meter of claim 1, wherein each of the stacked test strips has an outer edge, and wherein each of the outer edges is aligned with one another.

10. The test meter of claim 8, further comprising a seal extending between the interior cartridge housing and the outer housing.

11. The test meter of claim 1, wherein the cartridge further comprises an outer housing, the covering element configured to move along a length of an axis between the first position, wherein a bottom surface of the covering element joins with a surface of the outer housing to seal the cartridge closed, and the second actuated position, wherein the bottom surface of the covering element is spaced away from the surface of the outer housing.

12. The test meter of claim 1, wherein the dispensing member includes a notch and the covering element further comprises an opening sized to receive the notch, the opening configured to permit the notch to move within the opening when the covering element is moved from the first position to the second actuated position.

13. A cartridge for storing a plurality of stacked test strips in a test meter, the cartridge comprising:
    an outer casing;
    a covering element removably joined together with the outer casing, wherein the covering element is configured to move along a length of an axis between a first axial position, wherein at least a portion of the covering element is adjacent the outer casing, and a second axial position, wherein the at least a portion of the covering element is spaced away from the outer casing in the second axial position;
    a dispensing assembly seated within the outer casing, the dispensing assembly further comprising:
        a test strip storage area for storing the plurality of stacked test strips therein, each of the test strips having opposed edges aligned with one another; and
        a dispensing member movably connected to the covering element and configured to rotate between a first rest position and a second dispensing position, the dispensing member having a first end contacting a single test strip of the plurality of test strips and a second fixed end, the dispensing member configured to rotate about the fixed end; and
        a linear channel configured to allow movement of the free end there through, wherein the plurality of stacked strips is biased toward the dispensing member, and wherein when the covering element is moved away from the dispensing assembly, the dispensing member rotates about the fixed end and the free end of the dispensing member moves through the linear channel and moves the one test strip through an opening.

14. The cartridge of claim 13, wherein the at least a portion of the covering element is a bottom surface of the covering element, and wherein when the covering element is in the first axial position, the bottom surface of the covering element is closer to a receiving surface of the outer casing than when the covering element is in the second axial position and the bottom surface is joined with the receiving surface of the outer casing to seal the cartridge closed.

15. The cartridge of claim 13, wherein the dispensing member includes a notch and the covering element further comprises an opening sized to receive the notch, the opening configured to allow the notch to move within the opening when the covering element is moved from the first axial position to the second axial position.

* * * * *